United States Patent
Schwitalla et al.

(10) Patent No.: US 11,589,961 B2
(45) Date of Patent: Feb. 28, 2023

(54) IMPLANT MADE OF FIBRE-REINFORCED PLASTIC

(71) Applicants: Andreas Schwitalla, Berlin (DE); Wolf-Dieter Müller, Berlin (DE)

(72) Inventors: Andreas Schwitalla, Berlin (DE); Wolf-Dieter Müller, Berlin (DE)

(*) Notice: Subject to any disclaimer, the term of this patent is extended or adjusted under 35 U.S.C. 154(b) by 536 days.

(21) Appl. No.: 16/336,400

(22) PCT Filed: Nov. 14, 2017

(86) PCT No.: PCT/EP2017/079161
§ 371 (c)(1),
(2) Date: Mar. 25, 2019

(87) PCT Pub. No.: WO2018/087383
PCT Pub. Date: May 17, 2018

(65) Prior Publication Data
US 2019/0307534 A1    Oct. 10, 2019

(30) Foreign Application Priority Data
Nov. 14, 2016 (EP) .................................... 16198694

(51) Int. Cl.
*A61C 8/00* (2006.01)
*A61C 13/00* (2006.01)

(52) U.S. Cl.
CPC ........ *A61C 8/0016* (2013.01); *A61C 13/0004* (2013.01); *A61C 13/0006* (2013.01);
(Continued)

(58) Field of Classification Search
CPC .............. A61C 8/0016; A61C 13/0004; A61C 13/0006; A61C 13/0013; A61C 13/0018; A61C 13/0019
See application file for complete search history.

(56) References Cited

U.S. PATENT DOCUMENTS 5,181,930 A * 1/1993 Dumbleton ........... A61L 27/443
                                                          623/23.34
5,679,299 A * 10/1997 Gilbert ................ A61F 2/30907
                                                          156/148
(Continued)

FOREIGN PATENT DOCUMENTS

DE       10055465 A1    5/2002
DE    102013211175 A1   12/2014
(Continued)

OTHER PUBLICATIONS

European Search Report dated Apr. 21, 2017 for European Application No. 16198694 filed Nov. 14, 2016.
(Continued)

*Primary Examiner* — Nicholas D Lucchesi
(74) *Attorney, Agent, or Firm* — Blue Filament Law PLLC

(57) ABSTRACT

A customizable implant made of plastic including a thermoplastic which is reinforced with long fibers arranged multidirectionally in a targeted manner and has a modulus of elasticity E of 10-70 GPa is provided. A system for producing a customizable implant including a device for collecting patient data regarding the environment into which an implant is to be inserted, a computer program for creating a model for a customized implant based on the patient data collected, and a device for producing the customized implant based on the calculated model by means of 3D printing and/or laser sintering is also provided.

12 Claims, 4 Drawing Sheets

Figure 3:
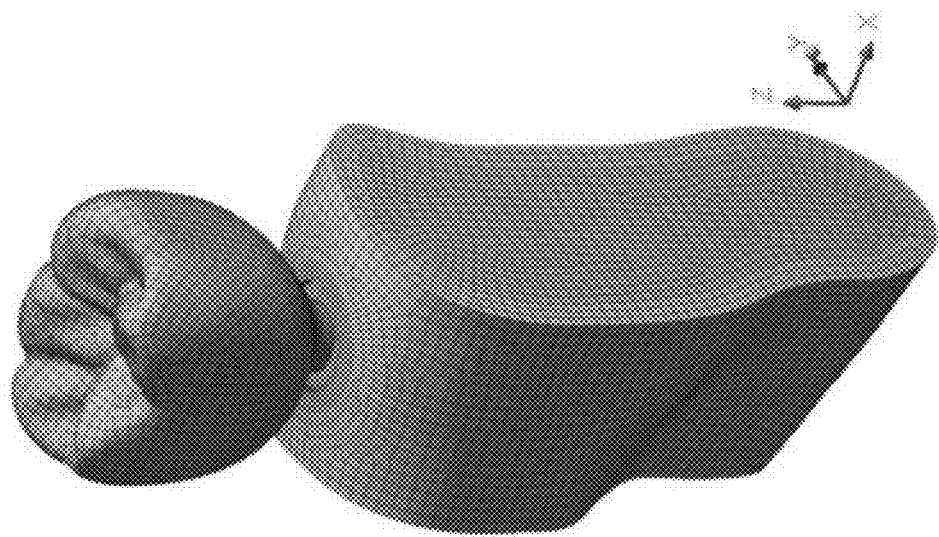

(52) U.S. Cl.
CPC ...... *A61C 13/0013* (2013.01); *A61C 13/0018* (2013.01); *A61C 13/0019* (2013.01); *A61L 2430/12* (2013.01)

(56) References Cited

U.S. PATENT DOCUMENTS

| | | | | |
|---|---|---|---|---|
| 5,915,970 | A * | 6/1999 | Sicurelli, Jr. | A61C 13/30 433/220 |
| 6,193,516 | B1 | 2/2001 | Story | |
| 6,987,136 | B2 * | 1/2006 | Erbe | A61L 27/446 424/423 |
| 9,451,873 | B1 * | 9/2016 | Kopelman | G06T 1/0007 |
| 2003/0148247 | A1 * | 8/2003 | Sicurelli, Jr. | A61C 13/30 433/220 |
| 2009/0061385 | A1 * | 3/2009 | Bahcall | A61C 8/0086 433/173 |
| 2009/0170054 | A1 * | 7/2009 | Spahn | A61C 8/001 433/173 |
| 2009/0287332 | A1 * | 11/2009 | Adusumilli | B33Y 50/00 700/98 |
| 2009/0317768 | A1 * | 12/2009 | Mayer | A61B 17/68 433/201.1 |
| 2010/0121463 | A1 * | 5/2010 | Tormala | A61L 27/48 623/23.75 |
| 2010/0274358 | A1 * | 10/2010 | Mueller | A61B 17/7059 623/17.16 |
| 2011/0008754 | A1 * | 1/2011 | Bassett | A61C 8/0012 433/175 |
| 2011/0086328 | A1 * | 4/2011 | Wedeking | A61C 8/00 433/174 |
| 2013/0071814 | A1 * | 3/2013 | Boehner | A61B 6/145 433/220 |
| 2013/0079829 | A1 * | 3/2013 | Globerman | A61B 17/7233 606/286 |
| 2013/0130203 | A1 * | 5/2013 | Velamakanni | A61K 6/20 433/222.1 |
| 2014/0335472 | A1 * | 11/2014 | Dosta | A61L 31/048 433/173 |
| 2016/0206786 | A1 * | 7/2016 | Ellman | A61L 27/06 |

FOREIGN PATENT DOCUMENTS

| | | |
|---|---|---|
| EP | 1598028 A1 | 11/2005 |
| EP | 2703141 A1 | 3/2014 |
| WO | 2005079696 A1 | 9/2005 |
| WO | 2007025782 A1 | 3/2007 |
| WO | 2014198421 A1 | 12/2014 |

OTHER PUBLICATIONS

English translation of International Search Report dated Jan. 17, 2018 for International Application No. PCT/EP2017/079161 filed Nov. 14, 2017.

* cited by examiner

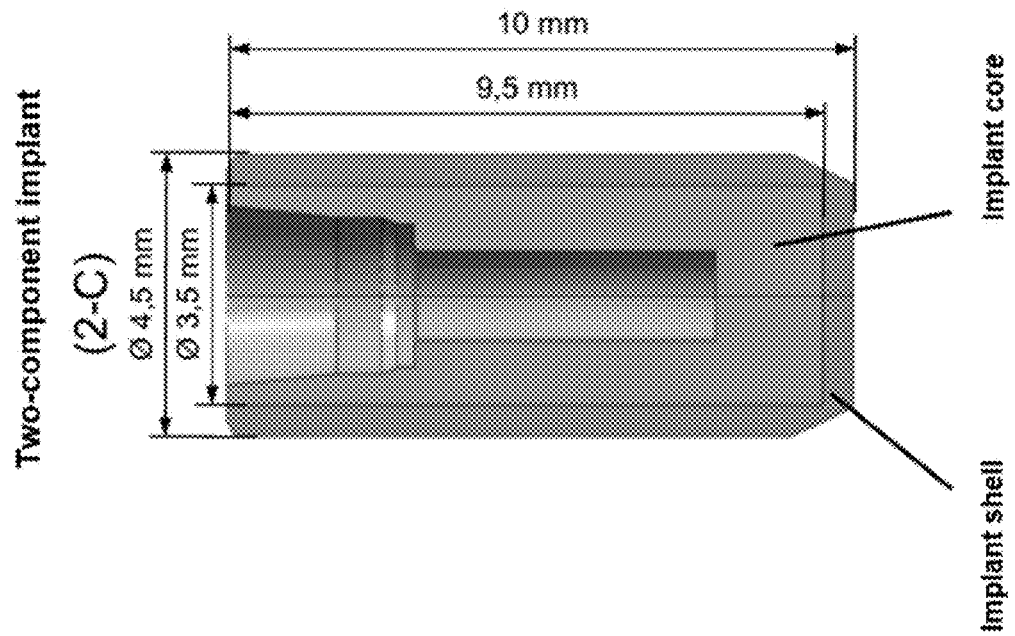
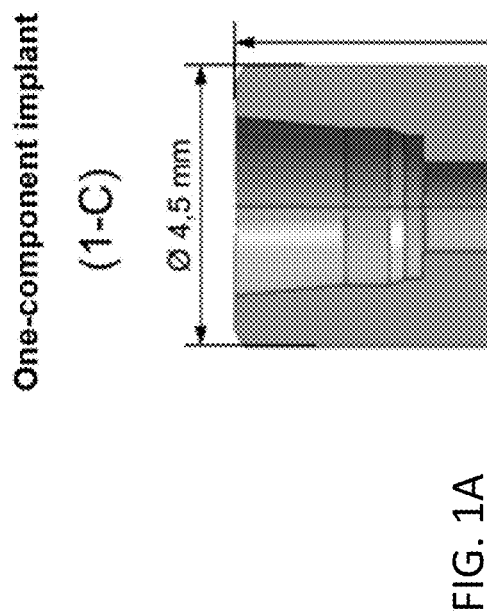
FIG. 1A
FIG. 1B

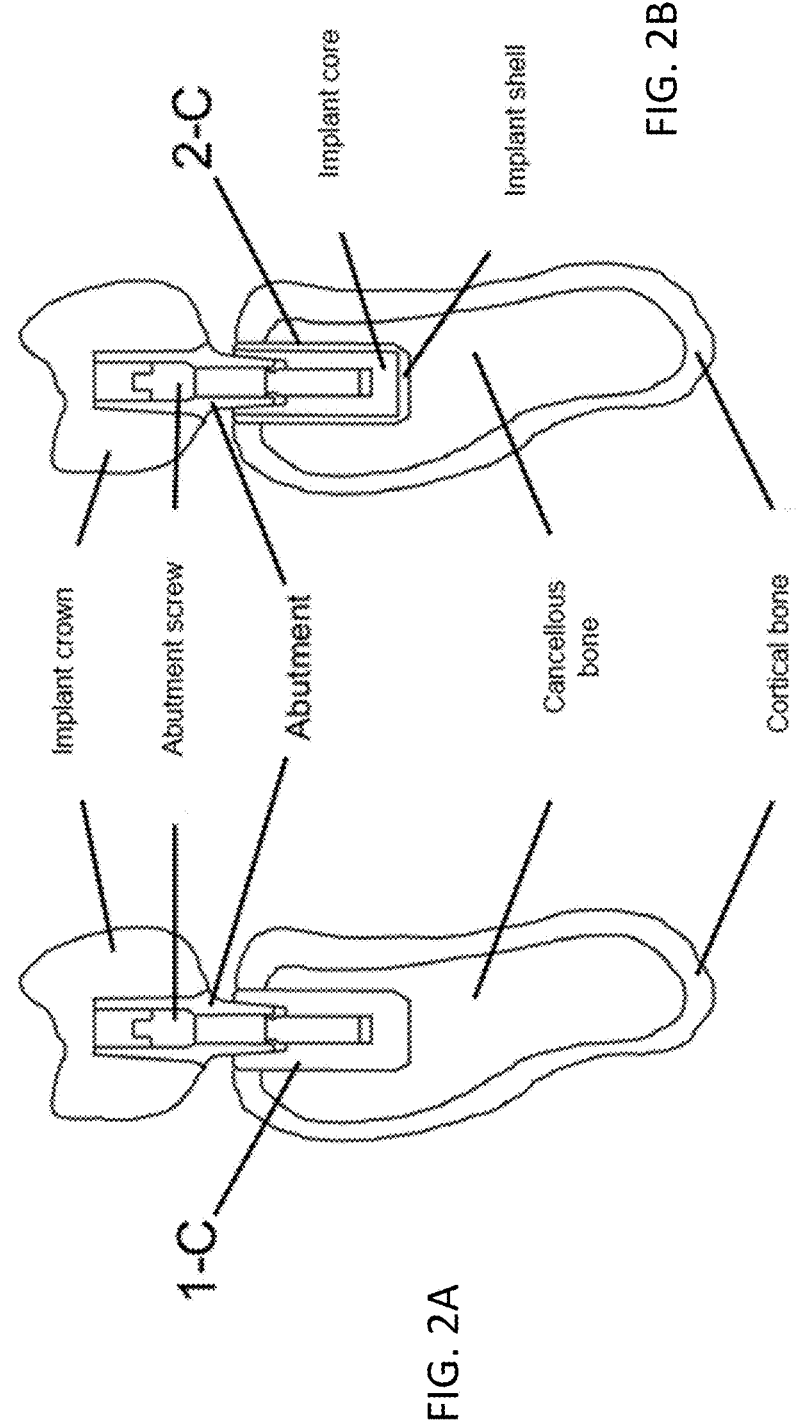

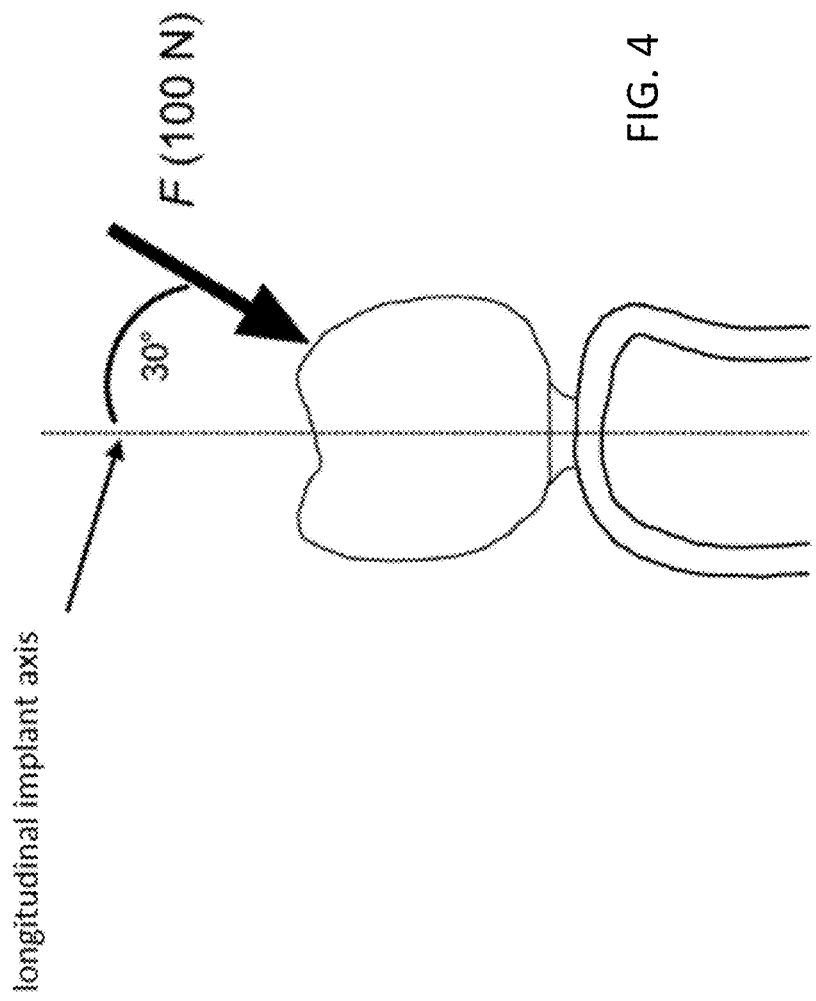

IMPLANT MADE OF FIBRE-REINFORCED PLASTIC

INTRODUCTION

The present invention relates to an implant made of plastic, characterized in that it includes a thermoplastic material which is reinforced with long fibers arranged multidirectionally in a targeted manner and has a modulus of elasticity E of 10-70 GPa. The present invention further relates to a system for producing an implant according to the invention, including a device for collecting patient data regarding the environment into which an implant is to be inserted, a computer program for creating a model for a customized implant based on the patient data collected, and a device for producing the customized implant based on the calculated model by means of 3D printing and/or laser sintering.

PRIOR ART

An implant is a synthetic material which is implanted into the body of a human being or an animal and connected to components of the skeleton therein and intended to remain there permanently or at least over a longer period of time. Implants are used when a natural tissue or natural material such as teeth, bones, or joints can no longer function due to disease, wear, or traumatic damage. Special embodiments of implants include, for example, dental implants, implants for osteosynthesis, such as osteosynthesis plates, spine cages and various types of joint replacements, such as endoprostheses, particularly for knee and hip joints.

Dental implants describe synthetic dental roots which are used in cases in which the tooth and/or the root are damaged or diseased. Dental implants have a helical or cylindrical design and are implanted into jaw bones to replace lost teeth. The dental implant takes over essentially the same function as the natural dental root because it integrates with the bone. In later phases of a treatment, the implant can be used to carry crowns or bridges, which represent a denture.

A dental implant consists of the implant body, which is inserted in the bone, and the build-up/abutment part, which is used to fasten the crowns or holding structures for prostheses to the implant body. A differentiation is made here between single or multi-part implants, in which the body and the abutment part are separated. But there are also implant systems in which the connecting element (abutment) to the dental prosthesis is integral with the implant body. It is also possible to screw the denture directly onto the implant body if, for example, the denture and the abutment are produced in one piece, as is the case for screwable dental crowns (screwed restorations). Furthermore, other components can be attached to the implant body, e.g. press studs ("locators"), magnets, or bridge structures.

Various materials selected from the groups of metals, ceramics, and plastics are nowadays used for producing implants. They all share the feature of long-term implantation approval due to proven biocompatibility.

Implants which are anchored in bony structures of the human skeleton are exposed to high mechanical loads and must therefore have respectively high moduli of elasticity and be stable. The modulus of elasticity (also called tensile modulus (of elasticity), elasticity coefficient, strain modulus, modulus E, or Young's modulus) is a material characteristic which describes the connection between stress and strain in the deformation of a solid body at linear elastic behavior. The modulus of elasticity is called in short modulus E or represented by the symbol E and has the unit of mechanical stress (Pascal/Pa). The amount of the modulus of elasticity is the greater the more resistance to elastic deformation a material exhibits.

Therefore, titanium and titanium alloys and ceramics such as zirconia have been predominantly used for this purpose. Titanium and zirconia have a high physical strength and low elasticity. A very elastic object (high elasticity) has a comparatively low modulus of elasticity. The moduli E of titanium and zirconia are 105 or 220 giga-Pascal (GPa), respectively.

The strength of material describes the maximum resistance to mechanical loads before it fails, that is, before an impermissible deformation, particularly a permanent deformation, or breakage occurs. Strength is indicated as mechanical stress (force per cross sectional area). Contrary to that, elasticity is the capacity of a body or material to change its form under the action of force and to return to its original shape when the application of force disappears.

If the prosthetic material or implant is made of one of these materials, the chewing forces which act on the prosthetic components of a dental implant, for example, are directly transmitted from the implant to the jaw bone via a rigid ankylotic connection. This is not the same as the natural action of forces during chewing, since the natural suspension of the tooth in the jaw bone is elastic, which allows a specific intrinsic mobility of the teeth. This natural tooth suspension subjects the tooth-bearing bone to tensile stress when the connective tissue fibers of the root membrane (desmodont) are tightened under chewing pressure.

When an implant made of titanium or zirconia is subjected to a load, the bone is subjected to compressive stress due to the rigid anchoring. In case of an overload, stress peaks can occur in the implant-bone interface, which can damage the bone and thus result in bone breakdown.

The use of very stiff materials for an implant can also produce a "stress shielding" effect. "Stress shielding" is defined as a reduction in bone density due to lack of the normal stress on the bone when it is bridged by an implant. The implant alone absorbs the normal stresses due to its high stiffness, and the adjacent bone is excessively protected. The use of implants having a very high stiffness, such as implants made of titanium or zirconia, in some regions can lead to a pathological remodeling of the bone tissue adjacent to the implant, which is accompanied by a loss in bone density and strength.

Due to the high stiffness and the low elasticity it entails, there is also a high risk of breakage for implants made of titanium and zirconia under high mechanical load.

Titanium has the additional disadvantage of having a high plaque affinity, which is particularly unfavorable when it is used as a dental implant. In addition, it is not possible to establish a bacteria-proof joint between a dental implant made of titanium and the prosthetic abutments used.

Furthermore, patients are nowadays interested in metal-free prostheses, particularly dental implants, also due to the dark color of titanium. Another disadvantage of titanium implants is the fact that some patients are oversensitive to titanium, which is why titanium implants cannot be used in these cases.

Therefore there is an increasing trend of using high-performance plastic materials such as polyether ether ketone (PEEK) for making implants, in addition to very stiff materials like titanium and zirconia. Since very high mechanical loads act on the implants after they were inserted in the body, particularly in the region of the anchoring structures, the high-performance plastic materials used for producing implants must often be mixed with reinforcing substances such as fibers, particularly carbon fibers.

Bone is an anisotropic material, on the one hand due to its mineralized structures which have various densities, in the cortical and particularly in the cancellous portions, on the other hand due to functional adjustments, for example to the trajectories which correspond to the greatest compressive and tensile stresses on the bone. At the same time, the mechanical properties of the jaw bone vary considerably from one individual to the other. Therefore, stress shielding effects and/or overload of the bone can occur even when using fiber-reinforced implants with particularly high moduli E. Vice versa, an implant which is not sufficiently fiber-reinforced be too elastic or insufficiently stiff, particularly in the cortical bone portion, which can also result in pathological bone remodeling.

Several implants have been described in prior art which consist of two or more materials having various degrees of hardness or moduli of elasticity to be easy on the adjacent bone. In most cases, a harder material is disposed in the interior while the exterior consists of a more elastic material.

U.S. Pat. No. 6,193,516 B1 describes implants which include a metallic core and an external shell made of a plastic material, wherein the plastic material can be PEEK continuously reinforced with carbon fibers. It says that the material properties of the plastic material can be adjusted by the length and orientation of the fibers. The implants described in U.S. Pat. No. 6,193,516 B1 particularly differ from the implants of the present invention in that they contain a metallic core and consist of multiple components. It is not specified what type of fibers is used, particularly with respect to the fiber thickness.

US 2009/061385 A1 describes fiber-reinforced dental implants made of PEEK, which consist of various interconnected components from different materials and with different degrees of hardness. The document does not describe, however, that the fibers in the implant or in the components of the implant have a specific orientation. The document therefore does not describe a targeted arrangement of the fibers inside the plastic material. The fiber-reinforced plastic material which the implant consists of is only defined by the modulus of elasticity. In addition, the fibers are not defined in detail with respect to their properties, such as their thickness. These implants therefore differ fundamentally from the implants of the present invention, which have surprising advantages over prior art implants due to a specific fiber arrangement and specific fiber thicknesses.

DE 102013211175 A1 proposes a reduction of the mechanical stress acting on the adjacent bone by implants produced from two interconnected plastic components, wherein a first plastic component having a similar modulus E as bones is disposed on the outside, and a second internal plastic component has a higher modulus E and gives the implant the necessary strength. The document proposes that the implants should be partially produced from PEEK reinforced with long fibers and having a modulus of elasticity of 20-80 GPa. DE102013211175 does not describe long fibers having a specific fiber thickness. It also merely discloses a parallel arrangement of long fibers, which differs from the multidirectional arrangement of the fibers in the implants according to the invention described herein.

EP 1 598 028 A1 describes an implant which includes an outer shell of metal and a core of plastic material, e.g. fiber-reinforced PEEK. The plastic component of the implant can be produced by means of the CFM method. This document also does not describe a multidirectional fiber arrangement, particularly no targeted multidirectional fiber arrangement. It also does not describe fiber properties, such as fiber thickness.

DE 10055465 A1 describes bone replacement materials, including materials made of PEEK, the modulus E of which can be adjusted by adding fiber-shaped filler particles, such as fibers or balls having a particle size of 0.1-200 µm. It is apparent that only reinforcement with short fibers is disclosed. In addition, the document describes the production of such implants by means of laser sintering using a CAD/CAM system. But it does not describe materials reinforced with long fibers, particularly not such materials in which the long fibers are multidirectionally arranged and have a specific diameter to achieve particularly good functionality. In addition, the materials according to DE 10055465 A1 have a lower modulus of elasticity than the plastic material of the implant according to the invention described herein.

It can generally be said about the prior art implants that these are all produced from multiple different materials or components which include an outer shell and a core. In most cases, one component is made of metal. It has also been found that these implants, particularly the implants according to DE 102013211175 A1 do not treat the implant-bone interface gently, contrary to their original purpose. On the contrary, it was found that increased elasticity of the outer layer at the implant-bone interface of respective implants results in an adverse load distribution to the surrounding bone, which leads to damage to the bone and sheathing of the implant by connective tissue.

Problem of the Invention

It is therefore the problem of the present invention to provide an implant which does not have the disadvantages of prior art described above. Accordingly, the problem is to provide an implant which is substantially metal-free, has the required stability to resist the mechanical stresses which act on an implant after insertion in the body, has a low risk of breaking and a low plaque affinity, allows bacteria-proof joining of the implant component and minimizes adverse mechanical stresses on the adjacent bone, such as stress shielding effects and overloads.

GENERAL DESCRIPTION OF THE INVENTION

According to the invention, the technical problem on hand is solved by providing an implant made of a plastic material, which includes a fiber-reinforced thermoplastic material having a modulus of elasticity E of 10-70 GPa.

In a preferred embodiment, the present invention relates to an implant made of plastic material, characterized in that it includes a thermoplastic material which is reinforced with long fibers arranged multidirectionally in a targeted manner and has a modulus of elasticity E of 10-70 GPa.

It was completely surprising to find that an implant made of a fiber-reinforced thermoplastic material having a modulus of elasticity of 10-70 GPa avoids adverse mechanical stress on the adjacent bone compared to prior art solutions. There are practically no stress shielding effects when using an implant according to the invention. This is ensured in that implants according to the invention, while they can resist the mechanical stresses due to their modulus of elasticity, they do not pass these stresses on unchanged to the adjacent bone, as is the case for considerably stiffer implant solutions made of titanium or ceramics. Instead, an implant according to the invention made of fiber-reinforced thermoplastic material can partially absorb the force acting on it by means of its elasticity.

On the other hand, there also is no unnatural load on the bone, as it occurs with implants made of thermoplastic materials without fiber reinforcement, the high elasticity of which results in non-physiological or pathological remodeling of the adjacent bone. Surprisingly, the fiber-reinforced thermoplastic materials having a modulus of elasticity of 10-70 GPa achieve an almost ideal balance between stiffness and elasticity compared to prior art implant solutions.

Due to these surprising mechanical properties of an implant according to the invention, mechanical forces are transmitted to the adjacent bone which are similar to those occurring under physiological conditions, for example when a healthy tooth and its natural suspension transmit forces.

The implant also has the necessary strength to resist the forces which act on the implant in the body under normal and high loads. At the same time, it has the necessary elasticity and flexibility that it will not break even under very high mechanical stress.

These advantageous mechanical properties described above and all other advantages of the invention mentioned herein particularly relate to implants according to the invention with long fiber reinforcement and a modulus of elasticity of 30-50 GPa. Surprisingly, these advantages are particularly prominent if the long fibers have a diameter of 4-10 µm and/or are arranged multidirectionally or arranged multidirectionally in a targeted manner.

In addition, it was surprisingly found that the advantageous mechanical properties of implants according to the invention mentioned herein can be further improved if these implants are made of only one component or of a uniform material.

According to a preferred embodiment, the implant according to the invention consists of a single component. A "single component" in the meaning of the invention means that the implant is made in a uniform process and not by first producing individual parts of the implement which are then joined together. This means that the implant according to the invention preferably consists of only one material. This material may comprise locally different compound additives or fiber arrangements, but it is a material produced in a uniform process.

Components in the meaning of the invention are particularly an implant core and a surrounding implant shell, which may consist of different materials having different (mechanical) properties.

The embodiment of the implant according to the invention differs in this respect from prior art implants, which are composed of a core and a shell and/or of different materials having different mechanical properties and are connected after producing the individual materials. The rationale of such implants made of multiple materials and/or components having different mechanical properties was that this could help reduce the stress on the adjacent bone. This hypothesis has not been confirmed as yet; it was found that particularly implants whose shell/outer layer is generally or indiscriminately reduced in hardness/elasticity compared to the core result in increased damage to the bone.

Contrary to that, the present invention showed that adverse bone remodeling effects can be reduced to a particularly great extent and sometimes do not occur at all if implants according to the invention made from only one component are used, which do not comprise indiscriminately different cores and shells. It was found instead that compound modifications in some sections, particularly (targeted) multidirectional arrangement of fibers, within an otherwise homogeneous component which is not divided into a shell and core or other parts have particularly positive effects on the maintenance and stability of the adjacent bone.

It is a great advantage of the implants according to the invention compared to titanium-based implants that the former do not corrode and therefore do not pose an increased corrosion-related risk of breaking.

Compared to known plastic implants having a higher elasticity, implants according to the invention have the advantage that they undergo less deformation under the mechanical stresses in the body. Elastic deformations in known plastic implants cause the implant surface to become porous, that is, to develop small cracks, indentations, and cavities, which facilitates settlement by microorganisms such as bacteria and fungi, which results in inflammation of the surrounding tissue and poses the risk of far-reaching health problems for the wearer of the implant through systemic spread of the infection. This risk does not exist due to the specific elastic properties of the implants according to the invention because deformations made possible by the specific modulus E are not severe enough that the implant surface could become porous.

It is a surprising advantage of the implant according to the invention that it can bend or be deformed just slightly under very high loads, which prevents the implant from breaking. At the same time, a portion of the force acting on the implant is absorbed and not transmitted to the bone, which is advantageous in terms of mechanical stress on the adjacent bone. It is particularly advantageous that this bending and deformation is completely reversible and that the implants according to the invention are returned to their initial state without any losses in function when the application of force ceases.

This is an advantage over known implants made of plastic material, which deform to a greater extent under high mechanical loads due to their higher elasticity compared to the implants of the invention, which can result in material failure. Implants according to the invention therefore have considerably longer use periods than known plastic implants, which must be replaced at regular intervals because they cannot resist the mechanical stresses permanently.

In addition, an implant according to the invention made of a fiber-reinforced thermoplastic material allows metal-free patient care. The specific elastic properties of an implant according to the invention having a modulus E of 10-70 GPa allow bacteria-proof connection with other prosthetic components, also under functional stress. This is not possible using known plastic implants, because these are too elastic and do not withstand functional stresses permanently, which results in a leaky joint.

A bacteria-proof joint is particularly important for two-part dental implants consisting of an implant body, which assumes the function of the root of the tooth, and an abutment, which acts as placeholder through the gingiva and carrier of the prosthetic crown. Bacteria-proof joining of metallic or ceramic components, whatever their geometrical shapes is not achievable. Remaining gaps will be permeable for bacteria. For example, bacteria which entered the internal screw duct of the implant body during the insertion of the implant can get to the outside through the joint with the abutment and cause inflammation at the interface area between bone, implant, and mucosa.

It is particularly horizontally acting forced which cause gaps to open up in the implant-abutment interface of multi-part implant variants made of titanium. This creates a type of pumping effect, which promotes bacterial colonization of the gap between implant body and abutment and presses exotoxins into the surrounding tissue.

The term "implant", in the meaning of this invention, refers to a synthetic material implanted into the body of a human or animal, where it is connected to components of the skeleton. Special embodiments of implants in the meaning of this invention include, but are not limited to, dental implants, implants for osteosynthesis such as osteosynthesis plates, spine cages (also called interbody fusion cages), suture anchors, various forms of joint replacement such as endoprostheses, particularly hip, shoulder, and knee joint prostheses, and prostheses for bridging bone defects, for example in the head and facial regions.

The term "dental implant" includes, but is not limited to, immediate implants, which have an anatomical shape corresponding to the existing alveolus or root of the removed tooth, and delayed implants, which have a round cross section corresponding to the diameter of the drill used for preparing the bone bed. Immediate implants and delayed implants can each be produced as one-piece dental implants which include an implant body, an abutment, and a dental crown in one integral component. Alternatively, they can each be produced as one-piece dental implants which include an implant body and an abutment in one integral component. In addition, immediate and delayed implants can be produced as two-piece dental implants in which implant body and abutment are separate components. The term dental implant further includes, but is not limited to, mini implants, hollow cylinder implants, blade implants, narrow jaw implants, disc implants, and subperiosteal implants.

In the context of the present invention, the term "plastic material" substantially refers to a material consisting of macromolecules. The respective macromolecules of a plastic material are polymers, which are composed of recurring base units. Plastic materials are divided in three large groups based on their physical properties: thermoplastic materials, duroplastic materials, and elastomers.

Thermoplastic materials, or thermoplastics, are synthetic materials which are deformable in a specific temperature range. It is advantageous that the implant according to the invention is molded from such a plastic material, since it allows adjustments with respect to the shape and condition of the implant by heating the material, such that any required shape changes can be made shortly before insertion. It is also possible that the shape of the implant adjusts to its specific surroundings if it is inserted in a heated state.

Another advantage results from the fact that thermoplastic materials can be processed by applying heat in a 3D printing method. This method ensures free design of the outer shape, regardless of injection molds the production of which requires great effort.

Thermoplastic materials can be divided into the groups of standard plastic materials, technical plastic materials, and high-performance plastic materials based on their mechanical, thermal, and chemical properties. Termoplastic materials include, but are not limited to, acrylonitrile butadiene styrene (ABS), polyamides (PA), polylactate (PLA), polymethyl methacrylate (PMMA), polycarbonate (PC), polyethylene terephthalate (PET), polyethylene (PE), polypropylene (PP), polystyrene (PS), polyether ether ketone (PEEK), polyether ketone ketone (PEKK), polyoxymethylene (POM), polyvinyl acetate (PVAC), thermoplastic polyurethane (TPU), polyaryletherketones (PAEK), and polyvinyl chloride (PVC).

It is a decisive advantage of the implant according to the invention that, by fiber reinforcement, the mechanical properties of the implant such as stiffness and elasticity can be adjusted to the mechanical requirements in a targeted manner.

Fiber-reinforced plastic materials (also called fiber-plastic composites) refers to materials which include both a plastic matrix and reinforcing fibers. The matrix encompasses the fibers, which are bound to the matrix by adhesive or cohesive forces. Fiber-plastic composites have a direction-dependent elasticity behavior due to the use of fiber materials. The highly specific strengths and stiffnesses of the reinforcing fibers cannot be utilized without the matrix material. A new construction material only results from a suitable combination of fiber and matrix materials. Mutual interaction of these two components imparts higher-value properties on this material than each of the two components involved would have alone. The mechanical and thermal properties of fiber-plastic composites can be adjusted, for example, through the selection of the fiber-matrix combination, the fiber angle, fiber volume fraction, layer sequence, fiber orientation, or fiber length.

Reinforcing fibers according to the invention disclosed herein include, but are not limited to, basalt fibers, boron fibers, glass fibers, ceramic fibers, silica fibers, steel fibers, aramid fibers, carbon fibers, polyester fibers, nylon fibers, polyethylene fibers, zirconia fibers, alumina fibers, silicon carbide fibers, and plexiglass fibers.

The modulus of elasticity (also called tensile modulus (of elasticity), elasticity coefficient, strain modulus, modulus E, or Young's modulus) is a material characteristic from materials engineering which describes the connection between stress and strain in the deformation of a solid body at linear elastic behavior. The term "modulus of elasticity" is called in short modulus E or represented by the symbol E and has the unit of mechanical stress. The amount of the modulus of elasticity is the greater the more resistance to elastic deformation a material exhibits. A component of a material with a high modulus of elasticity (e.g. titanium) is thus stiffer than a component of the same design (the same geometrical dimensions) which consists of a material with a lower modulus of elasticity (e.g. rubber).

It is also useful in the spirit of the present invention if the reinforcing fibers are long fibers. In another preferred embodiment of the invention, the reinforcing fibers are continuous fibers.

Advantageously, the implants according to the invention have demonstrated that stiffness and strength values of the implants according to the invention made of fiber-reinforced plastic increase with increasing length of the reinforcing fibers. Accordingly, plastic materials containing long fibers (>1 mm in length) achieve higher stiffness and strength values than plastic materials containing short fibers (<1 mm in length). The term "long fiber" as defined herein also includes continuous fibers having a length >50 mm. Continuous fibers are thus a special embodiment of long fibers.

Reinforcement of the implants of the invention with continuous fibers results in particularly high stiffness and strength values. Accordingly, implants according to the invention which are reinforced with long fibers, particularly with continuous fibers, are superior to implants without fiber reinforcement or implants reinforced with short fibers.

It is preferred that long fibers, particularly continuous fibers, are used for producing the implant according to the invention. The methods that were typical and common as yet for processing plastic materials containing long or continuous fibers are only with limitations suitable for producing implants according to the present invention. These methods mostly use a semi-finished product as parent material, which was produced by a pultrusion method and thus contains fibers arranged in parallel, and from which implants are produced by chip removal or milling.

Implants produced in this manner are only to a limited extent suitable for permanently resisting the mechanical forces which act on the implant from many different directions and different orientations during or after insertion in the body, since these only contain unidirectionally oriented fibers, which were in addition cut in the process of producing the implants from the semi-finished product. Examples of such acting forces include the tightening of fastening screws or in the case of dental implants the chewing forces which act on the implant when crushing food. It was therefore completely surprising that we succeeded, according to the invention, in producing implants from thermoplastic materials reinforced with long and/or continuous fibers, which implants can resist these mechanical stresses.

Another embodiment of the implant is characterized in that the fibers are arranged multidirectionally or unidirectionally.

A particularly preferred embodiment of the implant is characterized in that the fibers are arranged multidirectionally in a targeted manner or randomly multidirectionally.

In the context of the present invention, "unidirectional" fiber orientation means that all fibers contained in an implant according to the invention have the same parallel orientation. This results in a particularly high stability and tensile strength of the implant with respect to forces which act on the implant along the fiber orientation.

As defined in the present invention, "multidirectional" means that the fibers are not exclusively oriented parallel to each other but may extend in many different directions. There can be fibers which extend parallel to the longitudinal axis of the implant and fibers which extend at a right angle or obliquely to this axis, such that practically all conceivable fiber directions are possible. The fibers may also have a curved extension. Multidirectional fibers can have a random or targeted multidirectional orientation.

A "randomly multidirectional" arrangement (also called unoriented multidirectional arrangement) of the fibers means that the fibers do not extend parallel to each other inside the plastic matrix but form a random fiber mesh and thus virtually have all orientations possible inside the matrix. This is for example the result of producing fiber-reinforced plastic components using the CFM method.

Due to the production method, patterns or specific preferred arrangements of the fibers inside the component or implant may be formed. But this should still be considered a random multidirectional arrangement in the meaning of the invention, since this arrangement is not formed with respect to the forces that will later act on the implant and does not counteract such forces in a targeted manner. Instead, these arrangements are a random consequence of the production method.

The randomly multidirectional arrangement of the fibers in all areas of the implant including its thread increases the tensile strength of the material when forces act from all directions, since there always will be fibers that are stressed in the longitudinal direction and thus provide increased stability. Accordingly, implants according to the invention having a randomly multidirectional fiber orientation can withstand the manifold mechanical stresses they are exposed to better and more reliably than implants having a unidirectional fiber orientation.

A randomly multidirectional fiber orientation is for example advantageous compared to a unidirectional or parallel fiber orientation in the case of a dental implant having a male thread. When the fibers are arranged unidirectionally along the longitudinal axis of the dental implant, they cannot ensure reinforcement with respect to tensile and compressive forces acting along the longitudinal axis of the implant in the region of the thread flanks of the male thread used for anchoring the dental implant. If a strong tensile force acts on a respective dental implant inserted in the bone along its longitudinal axis, the thread flanks of the male thread represent the most likely breaking points of a respective implant, since the fibers do not provide reinforcement due to their orientation. This would be different in the case of a randomly multidirectional arrangement of the fibers, since the fibers also extend at an angle or perpendicular to the longitudinal axis of the implant, thereby causing a stabilizing effect, particularly in the region of the thread flanks.

A "targeted multidirectional" arrangement (also called multidirectionally oriented arrangement) of the fibers means that the fibers inside the plastic matrix of the implant according to the invention have a multidirectional arrangement which was designed and/or calculated in advance. The fibers are thus arranged or oriented in such a manner that they can ensure optimum stability taking into account the mechanical stresses that will act on the implant when in use.

Targeted multidirectional fiber orientation of an implant according to the invention ensures that the reinforcement of the mechanical properties, particularly the tensile strength, which is achieved by the fibers is effective against mechanical stresses in practically all areas of the implant. The fibers are oriented in such a manner that they optimally counteract particularly such forces which put vertical stress on the implant. In this way, forces that occur laterally are compensated as well. In addition, the fiber orientation in the implant can be adjusted to the local properties of the bone environment of the implant, which allows optimum, practically physiological, force transmission to the bone. Like the bone itself, a respective implant can in this way attain a specific anisotropy.

The multidirectional fiber arrangement can cause local anisotropies within the implant made of fiber-reinforced PEEK and generate tensile moduli/moduli of elasticity between approx. 100 GPa in the direction of the fibers and 3-4 GPa transversely to the fiber direction. Such moduli are needed to compensate locally different stresses.

A preferred embodiment of the implant according to the invention is characterized in that it includes a thermoplastic material which is reinforced with long fibers arranged multidirectionally in a targeted manner and which has a modulus of elasticity E of 10-70 GPa.

The designations or terms "multidirectionally arranged in a targeted manner" and "multidirectionally arranged" can be used synonymously for the purposes of the invention. This means that "multidirectionally arranged" has the same meaning in the context of the invention as "multidirectionally arranged in a targeted manner."

It was found that targeted multidirectional arrangement of the long fibers can prevent stress shielding effects on the adjacent bone. Due to the targeted fiber orientation, the stress on the bone corresponds to the stress that acts on the bone under physiological conditions. This can prevent pathological remodeling processes in the bone adjacent to the implant and in other tissues.

In a preferred embodiment of the implant according to the invention, the orientation of the fibers, the fiber content, the type of fibers and/or the fiber diameter differ(s) in sections within the implant. It is preferred that these local differences are due to a targeted fiber arrangement.

It is advantageous that, in this embodiment of the invention, the fiber orientation, the fiber content, the fiber composition and/or the fiber diameter within the implant in particular can be adjusted in a targeted manner to the respective mechanical stress in specific sections.

"Fiber composition" in the meaning of the present invention particularly refers to the composition of the fibers of various types of fibers, for example, carbon fibers, zirconia fibers, alumina fibers, silicon carbide fibers, or mixtures thereof. In addition, the term "fiber composition" refers to the composition of fiber bundles of individual filaments of one or multiple types of fibers.

For example, more fibers can be incorporated in regions of particular mechanical stress. The fiber orientation can also be oriented along the specific mechanical stress of the respective region, such that the implant can resist the forces acting there particularly well.

In a preferred embodiment of an implant according to the invention, for example, more fibers that extend at a right angle to the longitudinal axis of the implant can be incorporated in the region of a thread, such as a male thread which is used for anchoring the implant in the bone, and increase the stability of the thread in the event of tensile stress along the longitudinal axis of the screw. Furthermore, more fibers which follow the screw thread can be incorporated in the region of the thread flanks, which would result in reinforcement of the thread flanks under tensile stress along the longitudinal axis of the implant.

Surprisingly, this type of targeted use of reinforcing fibers can prevent the mechanical stress on the bone adjacent to the implant. For example, those regions of an implant according to the invention which do not undergo great mechanical stress, because they are not essential for anchoring the implant in the bone or for fastening abutments to the implant can be provided with lower stiffness by incorporating few or no reinforcing fibers in these areas. This would reduce transmission of force to the bone in these areas, since the adjacent plastic material of the implant is less stiff and easier deformable under force, such that a portion of the acting force is absorbed and the resulting transmission of force to the bone is similar to the physiological stress.

It is surprisingly possible to use targeted arrangement of reinforcing fibers in the various regions of the dental implant that border the bone to create mechanical stresses for the bone which are very similar to those caused by natural tooth suspension in the jaw bone. Such a design of the implant of the invention which is adjusted to the bone environment of the implant and the specific stresses which act on the implant thus generates an almost physiological stress for the adjacent bone and is highly advantageous compared to known implants.

The arrangement of the fibers in the implant must to this end be adjusted to the type of implant, the implantation site and the force acting on the implant there. For dental implants, it is important, among other factors, which tooth the implant is to replace and how stresses will act on the implant after insertion, for example during chewing.

A person skilled in the art knows how to obtain such load data for the respective implant type. Imaging methods which generate information about the spatial structures and the bone density of the environment where the implant is to be inserted can be used to this end, for example. Particularly suitable for this purpose are a digital volume tomograph (DVT) or computer tomograph (CT), which generate a DICOM (Digital Imaging and Communications in Medicine) record regarding the three-dimensional environment of the implant. In addition, patient parameters relevant for dental implants such as masticating force can be determined and recorded electronically. A person skilled in the art can process such information for example using a computer program to calculate the optimum fiber distribution in an implant according to the invention. A person skilled in the art can use this information to produce an implant according to the invention made of a fiber-reinforced thermoplastic material which comprises a different fiber distributions in different sections and is adjusted to the individual requirements with respect to the acting forces and the bone environment.

Furthermore, a person skilled in the art must distinguish an implant made of fiber-reinforced plastic material which contains a targeted multidirectional arrangement of long fibers from an implant which contains randomly multidirectionally arranged long fibers.

Targeted arrangement of the fibers in the implant produces a specific arrangement of the fibers in specific regions of the implant, resulting in a characteristic pattern of fibers arranged in a targeted manner in the implant. The fibers are specifically oriented in accordance with the stress lines/directions that occur after inserting the implant into the bone. This arrangement differs from a random arrangement, as it occurs, for example, when the implant is produced using an injection molding or CFM method.

A routine microscopic analysis or a similar analysis in which the arrangement of the fibers inside the implant can be made visible make it clearly identifiable if the fibers are arranged in the implant in a targeted manner or randomly. In a targeted arrangement, a very specific fiber arrangement can be found in specific regions of the implant, such as the apical end, which arrangement differs from the fiber arrangement in other regions of the implant. At the apical end, the implant is exposed to completely different mechanical loads than at its coronal end or at the center of the implant. This is reflected accordingly in the targeted fiber arrangement. The same applies to the outer layers compared to central layers.

Therefore, a differing, region-specific characteristic fiber arrangement can be found in the various regions of the implant as claimed according to the invention. It can depend on the later position of the implant in the jaw. Particularly, there can be fiber bundles which extend along the region-specific stress lines.

This is not the case if the fiber arrangement is random. In this case, the fibers arrange randomly, regardless of stresses that will later act on the implant. This may also create patterns or characteristic structures. But these are a result of the production process and do not reflect stress lines within the implant after insertion into the bone.

For example, fibers may be oriented along the outer contours of the screw thread when producing implants having a randomly multidirectional orientation, e.g. using the CFM method. This orientation must be considered random because it is created regardless of whether the screw thread is located at the apical or coronal end of the implant. The orientation is not based on the forces which are actually acting on the implant, but merely results from the production method.

Since specific production methods are also associated with specific fiber arrangements, these can clearly be distinguished from a targeted arrangement in which the fibers extend along characteristic stress lines of an inserted implant. Due to the fact that fiber patterns characteristic for the respective production method may also result from production methods which lead to a random fiber arrangement, it cannot even in a highly unlikely event happen that an implant produced by a method which results in a random fiber arrangement has the same fiber arrangement as an implant that has a targeted fiber arrangement. A person skilled in the art can therefore always distinguish implants having a targeted long fiber arrangement from implants having a random fiber arrangement.

In another embodiment of the implant according to the invention, the modulus of elasticity E is 20-60 GPa. It was found that implants according to the invention, particularly dental implants, which have a modulus of elasticity in the range from 20 to 60 GPa, are particularly advantageous because it was surprisingly found that such implants have a longer use life compared to implants with moduli E over 60 GPa or under 20 GPa.

In another embodiment of the implant according to the invention, the modulus of elasticity E is 30-50 GPa. Respective implants are particularly convenient for the wearer of the implant because the difference to the natural/healthy situation without an implant is not subjectively noticeable.

In another embodiment of the implant according to the invention, the modulus of elasticity E is 35-45 GPa. It was found for implants having a modulus E in the range from 35 to 45 GPa that these have particularly advantageous mechanical properties, such that there is no major modification of the adjacent bone even after a long time after the implant was inserted. This was particularly surprising for dental implants, since enamel, which represents the natural outer layer of teeth, has a modulus E of 50-85 GPa, which is higher than that of this embodiment of the implant according to the invention.

In another preferred embodiment, the implant is characterized in that the thermoplastic material is selected from a group including PEEK, PA, PE, POM, PMMA, PVAc, PU, and/or PAEK or polymer blends thereof or based thereon.

In another preferred embodiment, the implant is characterized in that the thermoplastic material is PEEK.

The polymer blends can be blends of two or more plastic materials, particularly of two or more biocompatible plastic materials, preferably of two or more biocompatible high-performance thermoplastic materials.

Such polymer blends can for example be selected from plastic materials of the group including PEEK, PA, PE, POM, PMMA, PVAc, TPU, PAEK, or polymer blends or plastic blends of one or more of these plastic materials with one or more other polymers or plastic materials, particularly other biocompatible polymers or plastic materials.

Polyether ketones (abbreviated PEK) are polymers in which ketone and ether functionalities occur alternately in their molecular backbone. The most common are polyaryletherketones (PAEK) in which an aryl group is linked in the 1,4 position between the functional groups. The very stiff backbone gives these materials very high glass transition and melting temperatures compared to other plastic materials. The most common of these high temperature resistant materials is polyether ether ketone (PEEK).

PEEK is a high temperature resistant thermoplastic material and belongs to the substance group of polyaryletherketones. PAEK and PEEK are resistant to almost all organic and inorganic chemicals and can withstand hydrolysis up to 280° C. In its solid state, PEEK can be milled, turned, or drilled. PEEK melts at a high temperature of 335° C. compared to other thermoplastic materials and can be molded by injection molding, 3D printing, CFM, compression molding or by means of an extruder. 3D fittings can be made from PEEK powders using lasers in the SLS method. This makes PEEK a particularly suitable material for producing implants, since it can be used in various processes which can be applied for producing implants according to the invention and is at the same time firm and resistant under physiological and pathological conditions which can occur in the body where the implants are inserted.

The use of PEEK as a material for producing implants is particularly advantageous due to its high strength and stiffness. It was found, according to the invention, that due to its modulus of elasticity of 3-5 GPa, this material is particularly well suited for making implants, since particularly advantageous properties can be achieved which are adjusted to the bone environment of the implant, particularly by adding reinforcing fibers and optionally other additives. Due to the good mechanical properties of PEEK, adjustment of its mechanical properties by compound additives and fibers is particularly simplified, and even small quantities of additives can have a significant effect. In addition, PEEK has a low density (1.32 g/cm3), which is very advantageous for producing the implants according to the invention, since the additional stress on the surrounding tissue and the patient who wears the implant is minimized.

Due to its good resistance to chemicals and stability with respect to solvents, PEEK is particularly suited for producing implants. In the insertion process, implants, particularly dental implants, frequently come into contact with chemicals and solvents, for example, when they are bonded together with prosthetic components which are built onto the implant. An implant made of PEEK has the decisive advantage that its shape and strength and other material properties do not change under the influence of the adhesives used, which contain various chemicals and solvents. Such resistance is beneficial for implants which come into contact with the outside world on body surfaces or accessible body regions, such as the oral cavity.

Another advantage of the implants according to the invention made of PEEK is their high resistance to radiation, particularly to UV rays. When bonding implants with prosthetic abutment components, UV radiation is often applied to cure the adhesive used. In this process, the implant is also exposed to the radiation. PEEK is therefore particularly suited for the production of implants, since other plastic materials become brittle and porous under the influence of radiation, particularly of UV rays.

Implants according to the invention made of PEEK have the advantage of being x-ray transparent, particularly when compared to implants made of metal, which is very beneficial in x-ray examinations and other imaging procedures performed on implant wearers, since the examination of the surrounding tissue is not impaired. Accordingly, implants of the invention do not have to be removed in a cumbersome process for such examinations, as is the case for example with implants made of metal.

Implants according to the invention made of PEEK also have the advantage of biocompatibility compared to known plastic implants, which can even be increased by the use of compound editors, particularly in the surface area of such an implant. In addition, implants made of PEEK are highly resistant to wear and abrasion, which is highly beneficial when used for dental implants, because these are exposed to strong frictional forces due to the chewing forces which act in the oral cavity. Implants according to the invention made of PEEK are also fiber-reinforced, which makes them particularly resistant to these forces. Contrary to that, known plastic implants cannot withstand these forces which act in the oral cavity and are therefore no equivalent functional alternative to the implants of the invention, particularly not as implants inserted for permanent tooth replacement.

In addition, implants made of PEEK have a very low plaque adherence, which can even be increased by adding suitable compound additives. This is particularly advantageous for application in dentistry, since plaque (dental plaque) which partially consists of microorganisms primarily settles on the surface of dental implants, which can result, for example, an inflammation of the surrounding tissue, dental cavities, periodontitis, and gingivitis. Known plastic implants which have an increased elasticity compared to implants according to the invention are particularly susceptible to plaque deposits because they quickly become porous, which additionally favors plaque deposition. Surprisingly, the risk of plaque deposition on the surface of implants of the invention made of PEEK could be minimized due to the interaction of plaque-repellent properties of PEEK, which can even be intensified by compound additives, and the mechanical properties of the implants of the invention, which [prevent] the formation of pores on the implant surface.

Another advantage of implants according to the invention made of PEEK is their low heat conductivity, which is particularly positive for dental implants, since the heat these implants are exposed to through contact with hot food in the oral cavity is not directly passed on to the bone, which could cause pain for the wearer of the implant. This is primarily a problem in prior art implant solutions made of metal.

In addition, implants made of PEEK have a low electrical conductivity, which lowers the risk that the wearer of the implant suffers severe health damage in the event of contact with a strong power source, particularly if compared to metallic implants.

Polyamides (PA) are linear polymers with periodically recurring amide bonds along the main chain. The amide group can be considered a condensation product of a carboxylic acid and an amine. The bond created in this process is an amide bond, which can be hydrolytically cleaved again. Polyamides are often used as construction materials because of their excellent strength and toughness. PAs show good chemical resistance to organic solvents, are cold resistant, resilient to shock, impact resistant, abrasion-proof even with a rough sliding partner, and have a high working capacity.

Polyethylenes (PE) are soft as wax and have an anti-adhesive surface. Polyethylenes our purest hydrocarbon. Like pure candle wax, they consist of hydrocarbon chains, only that the molecule chains in the polyethylene are longer. Polyethylenes have a low density, a good degree of toughness, and very good resistance to chemicals.

Polyoxyethylene (POM) is a highly molecular thermoplastic material and a universal plastic material which is often used for functional parts in precision mechanics and instrument construction. This construction material has excellent properties, for example a low resistance to friction, good abrasion resistance, excellent resilience, high resistance to fatigue and the changing load, good electrical properties, high dielectric strength, a low dielectric loss factor, good resistance to chemicals, particularly to solvents, and highly resistant to the formation of stress cracks.

Polymethyl methacrylate (PMMA) is a synthetic transparent thermoplastic material. PMMA is scratch resistant and of high optical quality. It is a high value transparent plastic material with a very high stiffness and good weather resistance.

Polyvinyl acetate (PVAc, sometimes just PVA) is a thermoplastic material from the group of polyvinyl esters which is synthesized by means of radical polymerization.

Thermoplastic polyurethane (TPU) is an elastic material with very good resistance to wear paired with a high level of resilient recovery.

The fiber-reinforced thermoplastic material preferably contains carbon fibers, zirconia fibers, alumina fibers, silicon carbide fibers, or mixtures thereof.

Carbon fibers in the meaning of the present invention are industrially produced fibers from carbon-containing parent materials, which are converted into carbon which is arranged like graphite through chemical reactions adjusted to the raw material. Isotropic and anisotropic types are distinguished. Isotropic fibers only have the low strength and lesser technical significance, and isotropic fibers show high-strength and stiffness and at the same time a low elongation at rupture in the axial direction.

Without limitation, the following carbon fibers are distinguished which can be used according to the present invention: HT (high tensity/high tenacity), UHT (ultrahigh tenacity), LM (low modulus), IM (intermediate modulus), HM (high modulus), UM (ultra modulus), UHM (ultra high modulus), UMS (ultra modulus strength), HMS (high modulus/high strength).

Typically, 1,000 to 24,000 filaments are combined into a multi-filament yarn (roving), which is coiled. The result is further processed into textile semi-finished products, such as fabrics, braids, or multiaxial structures on looms, braiding machines, or multiaxial warp knitting machines or in the field of producing fiber-reinforced plastic materials directly on pre-peg systems, pultrusion systems, or winding machines.

The use of carbon fibers for fiber-reinforcement of the thermoplastic material is highly advantageous for the present invention, since carbon fibers have a particularly high tensile strength of 3.5 to 4.5 GPa and a high tensile modulus of elasticity of 230-395 GPa, depending on the type of carbon fiber. These mechanical properties make it possible to provide the necessary stability to the thermoplastic material, which on its own would not be able to meet the mechanical requirements of an implant, by using carbon fibers for fiber reinforcement of an implant according to the invention.

Due to these specific mechanical properties, carbon fibers are particularly well-suited for adjusting the mechanical properties of the implant according to the invention to the forces which act on the implant in the body, such that the optimal balance between stiffness and elasticity can be set Especially the extraordinary tensile strength of 3.5-4.5 GPa makes it possible to significantly improve the tensile strength and stability of the thermoplastic material used by using just a relatively small portion of carbon fibers in the implant. The elongation at rupture of 1.1-1.5% is also advantageous when used according to the invention because it ensures a specific elasticity when strong forces act on the implant of the invention without impairing its stability.

Another important advantage of using carbon fibers in the context of the present invention is the particularly stable bond that can be generated between the reinforcing carbon fibers and the surrounding plastic matrix. This prevents shifting of the plastic material relative to the reinforcing fibers even under high mechanical stress on the implant. The mechanical properties of the carbon fibers are transferred to the implant according to the invention particularly efficiently by this particularly strong bond between the thermoplastic matrix and the carbon fibers.

In the context of this invention, a glass fiber is a long thin fiber consisting of glass. Thin threads are drawn from the glass melt to produce glass fibers. Glass fibers have a tensile strength of 1.8-5 GPa, a tensile modulus E of 70-90 GPa, and an elongation at rupture of 5%. Due to these mechanical and physical properties, glass fibers are particularly well-suited for processing as fiber reinforcement of implants according to the invention. Especially the high elongation at rupture of 5% allows the high elasticity of implants according to the invention which are reinforced with glass fibers. This is advantageous under extraordinarily high mechanical stress, since the implant can adjust its shape under such conditions without breakage of the reinforcing fibers. This also reduces the transmission of force onto the adjacent bone, thereby preventing pathological bone remodeling. At the same time, due to the high tensile strength, the implant is given the required stability to meet the requirements after insertion into the body.

Another important advantage of using glass fibers in implants according to the invention is that they are aging resistant and weather resistant, such that they can remain in the body over many years and thus virtually for a lifetime without losing their advantageous mechanical properties due to the moist environment, e.g. in the oral cavity in the case of dental implants. In addition, they are chemically resistant, such that the use of adhesives for fastening implant abutments will not cause impairment or damage to an implant reinforced with glass fibers.

In addition, the use of glass fibers, particularly for producing implants according to the invention which are visible from outside, such as dental implants, has the important advantage that they do not significantly change the optical appearance of a plastic material, which makes it easier to produce implants according to the invention in a color which is similar to that of teeth or bones if the fiber reinforcement is achieved using glass fibers.

According to the invention, zirconia fibers and alumina fibers are ceramic fibers made of an inorganic, non-metallic material which belong to the oxidic ceramic fibers. Due to their high tensile strength of 1.7-2.9 GPa and their highly variable and sometimes extremely high tensile modulus E of 15-370 GPa, these fibers are particularly advantageous as reinforcing fibers for implants according to the invention, since the mechanical properties of the implants are flexibly adjustable to the respective expected mechanical stresses in the body. Even if only a small percentage of fibers is used, highly stress-resistant implants can be produced. Due to their elongation at rupture of 0.6-1.1%, zirconia fibers and alumina fibers have the additional advantage when used in implants according to the invention that these also show some elasticity under high mechanical loads which allows some deformation of the implant before breakage occurs. This also reduces the transmission of force onto the adjacent bone, thereby preventing pathological bone remodeling. Due to their bright natural color, zirconia fibers and alumina fibers also make it easier to produce implants according to the invention in a tooth-like color, which is an optical advantage, particularly for applications in dentistry.

Silica carbide fibers according to the present invention (also called SIC fibers or nicalon) are produced from dichlorodimethylsilane. It is polymerized into polydimethylsilane, which rearranges into polycarbosilane when heated under condensation and with cleavage of chlorine. Fibers are drawn from this material, which are later pyrolyzed to form silicon oxycarbide fibers.

Silicon oxycarbide fibers (SIC fibers) can be used in the context of this invention for producing SIC fiber reinforced implants from a thermoplastic material. Such fiber reinforcement give the respective implants a very high fracture toughness, which is in the range of metals such as gray cast iron. This is primarily made possible by the high tensile strength of 2.6-3.4 GPa at a tensile modulus E of 170-420 GPa of the SIC fibers. In addition, silicon oxycarbide fibers have an elongation at rupture of 0.6-1.9%, which ensures some elasticity under very high mechanical loads and allows deformation of the implant before a break occurs. This also reduces the transmission of force onto the adjacent bone, thereby preventing pathological bone remodeling.

An important advantage of using SIC fibers is not only that they increase the fracture toughness of implants according to the invention, but also many optical properties, particularly an increase in translucence are enabled, which is particularly advantageous when used in dental implants.

In a preferred embodiment of the implant according to the invention, the reinforcing fibers have a diameter of 0.1 to 100 µm, preferably of 4 to 10 µm.

The diameter of a fiber, in the meaning of this invention, is its extension in a direction perpendicular to the axial direction.

According to the present invention, the reinforcing fibers can have different diameters, wherein an increased diameter is accompanied by higher resistance to wear and increased stability with respect to tensile stresses. The fibers may be composed of different types of fiber filaments and include nanoparticles which fuse with the fibers. The fibers can have a diameter of 0.1 µm up to 100 µm. The fracture toughness of the resulting composite material from which the implant according to the invention is produced can be considerably increased and adjusted specifically by the specific composition of the fibers.

A preferred embodiment relates to an implant made of a plastic material, characterized in that it includes a thermoplastic material which is reinforced with multidirectionally arranged long fibers and has a modulus of elasticity E of 30-50 GPa, wherein the reinforcing fibers have a diameter of 4 to 10 µm.

In another preferred embodiment, the implant of the inventions is made of a plastic material, characterized in that it includes a thermoplastic material which is reinforced with multidirectionally arranged long fibers and has a modulus of elasticity E of 30-50 GPa, wherein the reinforcing fibers have a diameter of 4 to 10 µm.

It was found that implants according to the invention into which fibers having a diameter in the range from 4 to 10 µm were incorporated are particularly advantageous, since such fibers can be processed well and can also be arranged in very fine structures of the implants according to the invention, such as in thread flanks. This is not that easily possible with fibers which have larger diameters. An important advantage of implants according to the invention having fibers with a diameter of 4 to 10 µm compared to implants having reinforcing fibers with smaller diameters is that the production method is significantly less complicated since the number of fibers to be incorporated is considerably lower if the fiber percentage is to be the same and if similar reinforcing properties are to be achieved.

Surprisingly, it was found that implants which have both a modulus of elasticity E in the range from 30-50 GPa and a diameter of 4-10 µm are particularly stable and resistant after being inserted into the bone. At the same time, it was completely surprising that the stresses on the bone by such implants were particularly low over very long periods of time, also compared to other implants disclosed herein which only have one of these features. Consequently, such implants have a particularly long durability after being inserted into the bone.

These special effects of good tolerability for the bone paired with resistance only occurred in this specific combination of features consisting of a modulus of elasticity of 30-50 GPa and fibers with a diameter of 4-10 μm. Negative stress shielding effects occurred on the adjacent bones when the modulus of elasticity was increased or decreased and fibers of 4-10 μm thickness were used. When thinner fibers were used, the fibers broke under permanent load, and such breaking occurred much earlier than when using fibers that were 4-10 μm thick. The fiber breakage was accompanied by a continuous decline of the modulus of elasticity and also resulted in damage to the adjacent bones.

When using thicker fibers with a diameter over 10 μm, it was found that under permanent load of the implants in the oral cavity, where they are also exposed to saliva enzymes, the implant surprisingly stiffened and the modulus of elasticity successively increased, which has a very adverse effect on the adjacent bones. The advantageous modulus of elasticity of 30-50 GPa could only be kept stable for long periods time and under load in the oral cavity when fibers with a diameter of 4-10 μm were used; these also allowed retaining the advantages of the invention for a very long time after inserting the implant. This is due to a surprising and unforeseen synergy effect of the specific fiber diameter of 4-10 μm and the specific modulus of elasticity of 30-50 GPa.

In one embodiment, the implant according to the invention is characterized in that the fiber content of the plastic material is 10-80% by volume, preferably 40-60% by volume.

In the meaning of the present invention, the fiber content is that volume fraction of the fiber-reinforced plastic material which is filled by fibers. The unit of the fiber content is percent by volume (vol %). The fiber content can be used to set specific mechanical properties of the implant according to the invention. A higher fiber content is accompanied by increased stability and fracture toughness.

It is advantageous that implants with a highly varying fiber content of 10-80 vol % may have suitable mechanical properties for an implant according to the invention because this allows for great design freedom in production. It was surprisingly found that a fiber content of 40-60% is particularly favorable for producing and any later shape adjusting of implants according to the invention.

In some embodiments of the invention, it can be advantageous that the fiber-reinforced thermoplastic material contains compound additives, preferably titanium dioxide ($TiO_2$), magnesium oxide, magnesium sulfate, hydroxyl apatite (HAP), tricalcium phosphate (TCP), bioglass, calcium sulfate, zinc phosphate, zinc oxide, and/or magnesium phosphate.

The term "compound additives" in the meaning of this invention refers to additional base materials (additives, composites), such as fillers, reinforcing agents, or other additives which are mixed into the plastic material in addition to the reinforcing fibers. Compounding is the process in which additives are combined with at least one base material into a homogeneous mixture.

The process for producing a compounded plastic material is called compounding. Compounding thus is a refining process of plastic materials by mixing in additives for targeted optimization of property profiles of plastic materials. Compounding is predominantly performed in extruders (primarily co-rotating twin-screw extruders, but also counter-rotating twin-screw extruders, planetary roller extruders, and co-kneader extruders) and includes, for example, such process operations as delivering, melting, dispersing, mixing, degassing, and pressure building. Thermoplastic materials can be compounded, for example, by means of twin-screw extruders.

The goals of compounding are manifold and depend on the desired properties of the later plastic material. An important goal of compounding according to the present invention is particularly the color setting of the fiber-reinforced thermoplastic material from which the implant according to the invention is made. This can be done by adding pigment particles to the fiber-reinforced thermoplastic material.

In addition, the mechanical properties of fiber-reinforced thermoplastic materials can be changed by adding compounds, including coloring pigment compounds. Compounds can also be used as processing aids, e.g. for making the demolding of the respective thermoplastic material in the injection molding process easier.

Additives, also called auxiliaries or excipients, are substances which are added to plastic materials to achieve or improve or modify specific properties. Additives are used to achieve a positive effect on production, storage, processing, or product properties during and after the use phase. Additives are typically optimized for the respective application.

In specific embodiments of the present invention, compound additives can for example be used to improve bone integration of the implant achieve reduce plaque affinity or provide that bacteria-repellent composition.

Such compound additives according to the invention can in particular be selected from a group including hydroxyl apatite, magnesium oxide, magnesium sulfate, $SiO_2$, $BaSO_4$, tricalcium phosphate tetracalcium phosphate, bioglasses (resorbable and/or stable calcium phosphate ceramics such as GB9, GB14, AP40), and $TiO_2$. The thermoplastic material can particularly be mixed with powdery compound additives, such as hydroxyl apatite, tricalcium phosphate, tetracalcium phosphate, barium sulfate, titanium dioxide, zinc oxide, and bioglasses (resorbable and/or stable calcium phosphate ceramics such as GB9, GB14, AP40).

In a particularly preferred embodiment of the present invention, the fiber-reinforced thermoplastic material includes the compound additive titanium dioxide. Adding titanium dioxide is advantageous in multiple respects. On the one hand, the implant according to the invention gets a bright color which is similar to that of Keith, even if it is reinforced with dark carbon fibers. On the other hand, titanium dioxide increases the biocompatibility of thermoplastic materials, particularly of PEEK, and enhances the integration of the implant into the bone.

Adding HAP also results in improved bone integration of the respective implant. Compound additives such as $BaSO_4$ can also result in an increase X-ray opacity.

In one embodiment of the present invention, the compound additives make up 0-20% of the overall weight (percent by weight, % (w/w)) of the fiber reinforced thermoplastic material, preferably 5-15% (w/w), particularly preferably 7-12% (w/w), particularly 10% (w/w). The powdery compound additives have a particle size of approx. 0.1-100 μm, preferably approx. 0.1-10 μm, particularly preferably of approx. 0.5-5 μm. Particles in the nanometer range have the advantage of increased biological effectiveness due to their maximum surface enlargement, wherein the influence the mechanical properties of the plastic matrix to a minimum metal extended only because of the small particle size.

In a preferred embodiment of the implant according to the invention, the fiber-reinforced thermoplastic material contains compound additives only in the surface area of the implant, down to a depth of approximately 200 µm.

"Surface area," in the meaning of the present invention, is the outer layer of the implant of the invention, which includes the outer surface of the implant and the region of the implant that extends inwards from the outer surface of the implant. The surface area defined in this matter therefore forms the outer cladding layer of the implant and has a layer thickness of up to 200 µm. This layer thickness is also called "depth" in the present invention.

It is particularly advantageous that the surface of the implant according to the invention can be changed by adding compound additives, such as titanium dioxide, such that for example the integration of the implant into the bone is made easier, the color of the implant can be adjusted to the wishes of the patient, or the x-ray opacity of the implant is changed favorably without changing the mechanical properties of the implant.

It has been found that implants which are made of two interconnected plastic components, wherein a first plastic component has a modulus E similar to that of bone is on the outside and has a layer thickness of >200 µm, and a second inner plastic component has a higher modulus E and gives the implant the required stability, induce an unfavorable distribution of load to the surrounding bone due to the increased elasticity of the outer layer. Excessive movement at the bone-implant interface are generated due to the large elastic self-deformation of the outer layer, which impairs osseointegration and can lead to implant loss. An example is explained in the specific description of the invention.

But it was surprisingly found that a change in composition of the material of an implant according to the invention in its surface area down to a depth of approx. 200 µm does not result in a change of the mechanical properties of the implant compared to an identical implant without this change in its surface area.

This gives rise to the surprising advantage that a manufacturer of an implant according to the invention is given great choice and flexibility in selecting the compound additives which are only intended to be used in the surface area of the implant according to the invention, for example to promote integration of the implant into the bone or to adjust the outside color of the implant, since there is no risk or need to consider that the respective compound additive could have an adverse effect on the mechanical properties of the implant. This gives the user greater freedom when selecting the composition of the material of the surface area to achieve the optimum properties for the respective application in this area.

In a preferred embodiment of the implant according to the invention the implant is a dental implant.

According to a preferred embodiment of the present invention, it is useful that the implant of the invention is produced in a 3D printing method and/or laser sintering method.

3D printing and particularly laser sintering allow the production of implants according to the invention made of fiber-reinforced plastic material, wherein the incorporation of long and continuous fibers is also possible.

In the 3D printing, implants according to the invention are built in layers. The buildup is computer-controlled from one or multiple liquid or solid materials based on specified dimensions and shapes (computer aided design/CAD). Physical or chemical curing or melting processes take place during buildup. Typical materials for 3D printing are plastic materials, synthetic resins, ceramics, and metals. In addition, thermoplastic materials and particularly high-performance plastic materials such as PEEK can be used in 3D printing, wherein these can at the same time variably be provided with fibers and compound additives.

Implants according to the invention that were produced using 3D printing have the advantage over implants made by injection molding that there is no need for elaborate production of molds and mold changing. The advantage compared to implants produced by material removal such as cutting, turning, milling, chip removal, or drilling is that there is no material loss in 3D printing, which is much more efficient and at the same time cost-saving. In addition, long and continuous fibers which are incorporated into the thermoplastic material of the implant according to the invention, remain undamaged in 3D printing, whereas these are part in material removal processes, which has an adverse effect on the mechanical properties of the implant according to the invention.

In addition, the process of 3D printing is energetically more advantageous than other production methods because the material is built only once with the required size and weight. Another strength of 3D printing is the option to build complex shapes of implants according to the invention, which are difficult to produce or cannot be produced at all on existing machinery. 3D printing also allows to produce customized implants, which are only needed for a specific one-time application, cost efficiently and fast, which is a great advantage over all other production methods.

Fiber-reinforced implants according to in the invention which were produced by 3D printing have the advantage that the base structures can be very delicate in design, because it is possible to arrange the fiber reinforcement with high precision. In addition, an implant according to the invention can be printed directly with compound additives (also called "coating composites") in their surface area by 3D printing, which results in a gapless connection between the coating composite and the plastic material. Adhesion between the two materials can additionally be increased by a plasma treatment of the plastic surface, which is integrated in the printer. A respective integrated plasma treatment can also be used to activate the surfaces of the incorporated fibers to improve the fiber-matrix composite.

3D printing technologies include, but are not limited to, selective laser melting, electron beam melting, selective laser sintering, stereolithography, digital light processing for liquid synthetic resins, and polyjet modeling as well as fused deposition modeling.

Laser sintering according to the present invention is a specific 3D printing method in which special structures are produced by sintering from the powdery parent material.

Laser sintering methods can be used for producing the implants according to the invention. Fine-grained materials, particularly thermoplastic materials, reinforcing fibers, and compound additives are heated, wherein increased pressure may be used as well. Laser sintering is a generative layer building method in which the implant according to the invention is built layer by layer. The laser beams can be used to produce any conceivable three-dimensional geometry including undercuts, such that implants having complex shapes can be produced, which could not be done by means of conventional mechanical or molding methods.

The basic prerequisite is that the three-dimensional geometry data of the implant to be produced are available and processed into layer data. For example, numerous layers are generated by "slicing" from existing CAD data of the implant to be produced (typically in STL format).

The powdery materials are placed flatly onto a construction platform using a doctor blade or roller at the thickness of 1-200 μm. The layers are sintered or molten into the powder bed by controlling the laser beam in accordance with the layer contour of the component. The construction platform is now slightly layered and a new layer is applied. The partners provided by lifting the powder platform or from a reservoir in the doctor blade. Processing takes place layer by layer in the vertical direction, whereby it is also possible to produce undercut contours on the implant according to the invention. The energy supplied by the laser is absorbed by the powder and results in localized sintering of particles while the overall surface area is reduced.

The plastic powders used here are typically not produced by grinding but are polymerized directly as beads, since the process places very high demands on the quality of the powder used, e.g. its pourability.

When producing implants according to the invention using a 3D printing method and/or laser sintering method, the reinforcing fibers can be arranged in a targeted manner and bundled and/or braided locally for optimum adjustment to the mechanical requirements. Continuous fibers, long fibers and/or short fibers can be incorporated into the thermoplastic material in a targeted manner at a specific orientation and varying between sections. The selection, arrangement, and condition of the printed fibers can depend on a predetermined composition and orientation which ensures optimal reinforcement of the implant. The underlying printing strategy can be additionally supported by a base which can be tilted in the X, Y, and Z directions and rotated about its axis, wherein the printer head can be moved in all axial directions to ensure ideal fiber furnish together with the plastic matrix. A targeted multidirectional fiber orientation can be achieved in this manner.

Regions of the implant which are under special stress, such as a female thread used for anchoring implant abutments, or a male thread used for anchoring the implant in the bone, can be reinforced through a specific fiber orientation or through region-specific adjustment of the fiber thickness. The 3D printing process also allows simultaneous admixture of compound additives, particularly in specific sections only, such as the surface area of the implant.

Unlike other production methods, 3D printing allows the customized and time-efficient production of implants, also based on individual records which provide information about the spatial environment and the forces which act there. The fiber orientation can be specifically determined in a targeted manner, whereby multidirectional orientation of the fibers and/or an orientation adjusted to the stress on the implant in specific sections can be achieved.

Respective 3D printers are known to a person skilled in the art. They contain mixer systems which allow feeding of multiple polymer components at various ratios to the printer head (gradient method). In this manner, different mechanical and physical properties can be implemented within a component in one printing process.

A great advantage of producing implants by 3D printing is the option to produce customized implants for a patient directly at the treatment site, e.g. in a hospital or doctor's practice, by means of an available 3D printer. After collecting the individual patient data, particularly with respect to the spatial environment of the implant, the bone density in the areas adjacent to the implant, and the forces which act on the implant, e.g. chewing forces in the case of dental implants, this data can be used to produce a customized implant by 3D printing on site and to insert it directly. This makes it possible, for example, to produce and insert a dental implant customized according to the invention for a specific patient during a single session at the dentist's office.

In another preferred embodiment of the invention, the implant according to the invention was produced by a CFM method or a compression molding method.

The CFM method (CFM=composite flow molding) is a high-pressure molding method in which a composite material (typically part of a pultruded rod), mostly reinforced by long or continuous fibers arranged in parallel, preferably a fiber-reinforced thermoplastic material, particularly preferred carbon fiber-reinforced PEEK, is converted directly by heat and pressure into the shape of the object to be produced, for example an implant according to the invention.

In the CFM method, a semi-finished PEEK product which was produced by a pultrusion method is caused to melt by exposure to heat and pressed by a plunger into a casting mold. This results in a randomly multidirectional arrangement of the fibers in the component produced. In small components, such as dental implants, the positive mechanical effects which result from a multidirectional fiber arrangement for the stability of the component are leveraged particularly well.

Unlike injection molding, the CFM method allows processing of fiber-reinforced thermoplastic materials such as PEEK with continuous fibers, and the resulting implant therefore has advantageous properties with respect to its strength and modulus of elasticity. The fibers arrange randomly inside the screw, such that multidirectional fiber orientation is ensured.

Surprisingly, there is also an additional, specific, continuous orientation of the fibers along the outer contours of the implant, e.g. withing thread structures. This gives the implant particularly high tensile strength and stability, e.g. in the region of optionally provided thread flanks, which ensures permanent stability of such an implant in the installed state. At the same time, the fibers are protected from abrasion through their firm embedding in the matrix.

The compression molding method is a manufacturing method for plastic materials which can process fiber-reinforced thermoplastic materials. At the beginning of the process, the fiber-reinforced thermoplastic material is introduced into a cavity which is heated to melt the plastic material. Then the cavity is closed using a plunger. The pressure gives the plastic material the shape determined by the cavity, e.g. that of an implant. After cooling down, the component can be removed from the mold and optionally be post-processed or further processed.

It was surprising that such delicate components as implants, particularly dental implants, made of fiber-reinforced thermoplastic material can be produced by compression molding. Implants made by compression molding have the advantage that they can be produced fast and in large quantities. In addition, implants produced by compression molding have a multidirectional fiber arrangement which contributes to their specific mechanical resistance and stability. Surprisingly, production by compression molding results in a particularly high stability of thread flanks provided on the implant, which are otherwise particularly unstable under stress.

In another preferred embodiment of the invention, the implant according to the invention was produced by a braiding method, wherein the reinforcing fibers are placed as a braided fiber arrangement onto a shape-imparting core and then enclosed by plastic material. Multiple layers of braided long fibers can be placed one after the other onto a shape-imparting core made of PEEK, such that the implant grows layer by layer and each layer has a specific fiber arrangement. Starting from a small shape imparting core, the implant can be built in layers, in that braided fiber layers placed onto the core are enclosed by the PEEK layer onto which the next layer of braided fibers can then be placed.

Implants produced by this method are particularly advantageous because each braided layer can have a specific fiber arrangement, enabling adjustment of the mechanical properties in specific sections.

The breathing technique can be used to produce complex structures, such as finest surgical threads or medical stents. The filament angle during braiding can be preset. This allows the production of tailor-made operated product. The breathing technique is an efficient production method which can easily be automated and provides high flexibility. Since the bread can be placed following the contour on a shape importing core, the breeding method is a technology that produces little waste and requires virtually no draping. In addition, it benefits from the adjustable filament angles for absorbing torsional and thrust loads.

In another preferred embodiment of the invention, the implant according to the invention was produced by filament winding method. The filament winding method can be used to produce implants according to the invention which are reinforced by continuous long fibers or continuous fibers. In this method, heated product from pre-impregnated fibers is wound multiple times around a rotating metal spike, for example in an overlapping helical pattern, to produce a layered cylinder having a preferred fiber structure. It is also possible to adjust the fiber arrangement during winding in a targeted manner to the respective position within the implant.

The pre-impregnated product is heated to a temperature above the melting temperature of the thermoplastic material used and joined with the underlying wrapped material by means of an application head. When the intended number of fiber layers has been applied in the intended predetermined orientation and positioning, the spike is pulled out, such that a hollow cylinder implant according to the invention is obtained made of the thermoplastic material which was reinforced with fibers in a targeted manner. Another option is to use a prefabricated cylindrical component which is to form the core of an implant according to the invention as a spike in the filament winding method, which spike is not removed thereafter. Winding with pre-impregnated fibers creates a reinforcement which ensures resistance proportional forces and provides stiffness. In addition, splitting of the implant is prevented when it is unfavorably stressed, e.g. drilled into from outside.

Furthermore, the present invention relates to a system for producing an implant according to the invention, including:
  a device for collecting patient data regarding the environment into which an implant is to be inserted, particularly including data about
    the force applied under mechanical stress,
    the bone density, and/or
    the spatial structure of the environment,
  a computer program for creating a model for a customized implant based on the patient data collected, wherein
    the three-dimensional structure of the implant,
    the material composition including a thermoplastic material, reinforcing fibers, and/or compound additives, and
    the arrangement of the reinforcing long fibers and optionally of the compound additives is calculated,
  a device for producing the customized implant based on the calculated model by means of 3D printing and/or laser sintering.

In a preferred embodiment, the invention relates to a system for producing an implant according to the invention having a modulus of elasticity E of 30-50 GPa, including:
  a device for collecting patient data regarding the environment into which an implant is to be inserted, wherein the collected patient data particularly include
    the force applied under mechanical stress,
    the bone density, and/or
    the spatial structure of the environment,
  a computer program for creating a model for a customized implant based on the patient data collected, wherein
    a three-dimensional structure of the implant,
    a material composition including a thermoplastic material, reinforcing long fibers having a diameter of 4 to 10 μm, and, optionally, compound additives, and
    a multidirectional arrangement of the reinforcing long fibers and optionally of the compound additives are calculated, and
  a device for producing the customized implant based on the calculated model by means of 3D printing and/or laser sintering.

A "system" in the meaning of the present invention is a totality of elements which are needed for the production of an individual implant, which elements are related and connected to each other, and interact, in such a manner that they can be considered a unit for producing an implant according to the invention.

The device for collecting patient data can for example be a measuring instrument with which the patient data is collected and stored. In another embodiment, this device can also be a data carrier on which data which has been collected previously using other devices, is stored and in this manner captured. Such devices particularly include computer hard disks, but also other computer readable storage media or data carriers.

The data provided by the device for collecting patient data is processed by a computer program within the system of the invention, whereby a model of a patient-specific implant according to the invention is created based on this data. Such a model describes the three-dimensional structure of the implant, wherein the patient data regarding the spatial structure of the environment into which the implant is to be inserted is taken account for creating this structure.

In addition, the material composition including a thermoplastic material, which can also be a blend of two or more plastic materials, reinforcing fibers, and compound additives is taken into account in the model created. When selecting the material composition, the computer program takes into account the collected patient data to calculate the optimum composition for the specific situation in which the implant to be produced is intended to be used.

In the model of the implant created by the computer program, the positioning and orientation of the reinforcing fibers within the implant are also taken into account. This particularly includes the distribution of the reinforcing fibers, the fiber composition, the fiber diameter, and/or the fiber density in the various regions of the implant. Based on the patient data, the computer program can calculate the regions in which the implant needs particular reinforcement for increased stability and the regions where it is advantageous to use less reinforcing material in order to increase flexibility.

When creating the implant model, the computer program further considers which compound additives are to be used and in which regions of the implant these additives are to be used. Compound additives can be incorporated throughout the implant to influence the overall properties of the implant.

Alternatively, specific compound additives may only be used in the surface area of the implant, for example to create a color coverage or to facilitate bone integration of the implant after insertion without changing the mechanical properties of the fiber reinforced thermoplastic material used.

Any type of 3D printer can be used as device for producing the customized implant based on the calculated model, particularly such printers which use fused deposition modeling (FDM), stereolithography (SLA), multi-jet modeling (MJM), selective laser sintering (SLS), selective laser melting (SLM), selective electron beam melting (SEBM), and/or 3-dimensional printing (3DP by Zcorp.).

The system according to the invention has the advantage that the customized implant of the invention, which is adjusted to the patient-specific requirements, can be produced within a short period of time. This largely avoids the disadvantages of existing implant solutions. Particularly, negative mechanical stresses on the adjacent bone and the risk of breaking can be minimized in this manner. In addition, targeted use of compound additives, particularly in the surface area of the implant, can achieve targeted color adjustment of the implant, reduce plaque adherence, and incorporated a bacteria-repellent surface. Furthermore, the mechanical condition of the implant can be designed such that the bacteria-proof joint with components to be connected to the implant is possible.

Sometimes the system can be used to produce all PEEK-based tooth replacement variants, from a single tooth crown to a bridge construction to entire partial and full prostheses. By means of an additional printing head especially for coating composites and/or compound additives, fiber-reinforced PEEK structures can be coated with a printable dental composite or compound additives, such that these structures are given the appearance of natural teeth.

Furthermore, the present invention relates to a device for producing an implant according to the invention, including:
- a unit for collecting patient data regarding the environment into which an implant is to be inserted, particularly including data about
  - the force applied under mechanical stress,
  - the bone density, and/or
  - the spatial structure of the environment,
- a unit for creating a model for a customized implant based on the patient data collected, wherein
  - the three-dimensional structure of the implant,
  - the material composition including a thermoplastic material, reinforcing fibers, and/or compound additives, and
  - the arrangement of the reinforcing long fibers and optionally of the compound additives is calculated,
- a unit for producing the customized implant based on the calculated model by means of 3D printing and/or laser sintering.

In a preferred embodiment, the invention relates to a device for producing an implant according to the invention having a modulus of elasticity E of 30-50 GPa, including:
- a unit for collecting patient data regarding the environment into which an implant is to be inserted, wherein the collected patient data particularly include
  - the force applied under mechanical stress,
  - the bone density, and/or
  - the spatial structure of the environment,
- a unit for creating a model for a customized implant based on the patient data collected, wherein
  - a three-dimensional structure of the implant,
  - a material composition including a thermoplastic material, reinforcing long fibers having a diameter of 4 to 10 µm, and, optionally, compound additives, and
  - a multidirectional arrangement of the reinforcing long fibers and optionally of the compound additives are calculated, and
- a unit for producing the customized implant based on the calculated model by means of 3D printing and/or laser sintering.

According to the invention, a device particularly is a gadget, apparatus, or unit which may be composed of different partial gadgets, apparatuses, or units, which together allow the production of an implant according to the invention.

The device according to the invention includes a partial device or a unit for collecting patient data, such as a measuring instrument, by means of which patent data can be collected and stored, or a data carrier on which data collected previously using other devices are stored and thus captured. Such devices particularly include computer hard disks, but also other computer readable storage media or data carriers.

The data provided by the unit for collecting patient data is used within the device according to the invention by a second device for creating a model for a customized implant based on the patient data collected, whereby this device creates a model of a patient-specific implant according to the invention based on this data. Such a model describes the three-dimensional structure of the implant, wherein the patient data regarding the spatial structure of the environment into which the implant is to be inserted is taken account for creating this structure.

In addition, the material composition including a thermoplastic material, which can also be a blend of two or more plastic materials, reinforcing fibers, and compound additives is taken into account in the model created.

In the model of the implant, the positioning and orientation of the reinforcing fibers within the implant are also taken into account. This particularly includes the distribution of the reinforcing fibers, the fiber composition, the fiber diameter, and/or the fiber density in the various regions of the implant. Based on the patient data, the unit for creating the model can calculate the regions in which the implant needs particular reinforcement for increased stability and the regions where it is advantageous to use less reinforcing material in order to increase flexibility or elasticity.

When creating the implant model, the device of the invention further considers which compound additives are to be used and in which regions of the implant these additives are to be used. Compound additives can be incorporated throughout the implant to influence the overall properties of the implant. Alternatively, specific compound additives may only be used in the surface area of the implant, for example to create a color coverage or to facilitate bone integration of the implant after insertion without changing the mechanical properties of the fiber reinforced thermoplastic material used.

Any type of 3D printer can be used as device for producing the customized implant based on the calculated model, particularly such printers which use fused deposition modeling (FDM), stereolithography (SLA), multi-jet modeling (MJM), selective laser sintering (SLS), selective laser melting (SLM), selective electron beam melting (SEBM), and/or 3-dimensional printing (3DP by Zcorp.).

The device according to the invention has the advantage that the customized implant of the invention, which is adjusted to the patient-specific requirements, can be produced within a short period of time. This largely avoids the disadvantages of existing implant solutions. Particularly, negative mechanical stresses on the adjacent bone and the risk of breaking can be minimized in this manner. In addition, targeted use of compound additives, particularly in the surface area of the implant, can achieve targeted color adjustment of the implant, reduce plaque adherence, and incorporated a bacteria-repellent surface. Furthermore, the mechanical condition of the implant can be designed such that the bacteria-proof joint with components to be connected to the implant is possible.

Sometimes this device can be used to produce all PEEK-based tooth replacement variants, from a single tooth crown to a bridge construction to entire partial and full prostheses. By means of an additional printing head especially for coating composites and/or compound additives, fiber-reinforced PEEK structures can be coated with a printable dental composite or compound additives, such that these structures are given the appearance of natural teeth.

Furthermore, the present invention relates to a method for producing an implant according to the invention, including:
collecting patient data regarding the environment into which an implant is to be inserted, particularly including data about
the force applied under mechanical stress,
the bone density, and/or
the spatial structure of the environment,
creating a model for a customized implant based on the patient data collected, wherein
the three-dimensional structure of the implant,
the material composition including a thermoplastic material, reinforcing fibers, and/or compound additives, and
the arrangement of the reinforcing long fibers and optionally of the compound additives is calculated,
producing the customized implant based on the calculated model by means of 3D printing and/or laser sintering.

In one embodiment, the invention relates to a method for producing an implant according to the invention having a modulus of elasticity E of 30-50 GPa, including:
collecting patient data regarding the environment into which an implant is to be inserted, wherein the collected patient data particularly include
the force applied under mechanical stress,
the bone density, and/or
the spatial structure of the environment,
creating a model for a customized implant based on the patient data collected, wherein
a three-dimensional structure of the implant,
a material composition including a thermoplastic material, reinforcing long fibers having a diameter of 4 to 10 μm, and, optionally, compound additives, and
a multidirectional arrangement of the reinforcing long fibers and optionally of the compound additives are calculated, and
producing the customized implant based on the calculated model by means of 3D printing and/or laser sintering.

The method according to the invention is a method for producing an implant according to the invention. As part of this method, patient data is collected and stored, for example using a measuring instrument. In another embodiment of the method, the patient data can also be provided and captured by a data carrier on which previously collected patient data is stored.

The collected patient data is used in another step of the method according to the invention for creating a model for a customized implant, for example by a computer program. Such a model describes the three-dimensional structure of the implant, wherein the patient data regarding the spatial structure of the environment into which the implant is to be inserted is taken account for creating this structure.

In addition, the material composition including a thermoplastic material, which can also be a blend of two or more plastic materials, reinforcing fibers, and compound additives is taken into account in the model created. Furthermore, the positioning and orientation of the reinforcing fibers within the implant are also taken into account. This particularly includes the distribution of the reinforcing fibers, the fiber composition, the fiber diameter, and/or the fiber density in the various regions of the implant.

After creating the model of the customized implant according to the invention, a customized implant is produced in another step of the method according to the invention. Any type of 3D printer can be used for this purpose, particularly such printers which use fused deposition modeling (FDM), stereolithography (SLA), multi-jet modeling (MJM), selective laser sintering (SLS), selective laser melting (SLM), selective electron beam melting (SEBM), and/or 3-dimensional printing (3DP by Zcorp.).

The method according to the invention has the advantage that the customized implant of the invention, which is adjusted to the patient-specific requirements, can be produced within a short period of time. This largely avoids the disadvantages of existing implant solutions. Particularly, negative mechanical stresses on the adjacent bone and the risk of breaking can be minimized in this manner. In addition, targeted use of compound additives, particularly in the surface area of the implant, can achieve targeted color adjustment of the implant, reduce plaque adherence, and incorporated a bacteria-repellent surface. Furthermore, the mechanical condition of the implant can be designed such that the bacteria-proof joint with components to be connected to the implant is possible.

Sometimes this method can be used to produce all PEEK-based tooth replacement variants, from a single tooth crown to a bridge construction to entire partial and full prostheses. By means of an additional printing head especially for coating composites and/or compound additives, fiber-reinforced PEEK structures can be coated with a printable dental composite or compound additives, such that these structures are given the appearance of natural teeth.

SPECIAL DESCRIPTION OF THE INVENTION

Figures:

FIGS. 1A and 1B:

show a longitudinal section through a one-component implant (1-C) made of 55-CFR-PEEK and a two-component implant (2-C) which consists of an implant core made of 55-CFR-PEEK and an implant shell surrounding the core made of a titanium oxide filled PEEK.

FIGS. 2A and 2B:

show the structure of the models for a 1-C and 2-C implant, each of which being embedded in the bone segment of a lower jaw, which consists of a cortical bone layer and a cancellous bone portion, which were supplemented with an abutment, an abutment screw, and an implant crown.

FIG. 3:

shows the predominantly hexahedral finite element mesh.

FIG. 4:

shows the introduction of a load of 100 N according to ISO 14801:2007 at 30° to the longitudinal axis of the implant.

EXEMPLARY EMBODIMENTS

A finite element analysis was performed to examine the mechanical effects on the peri-implant bone when exposing a PEEK implant reinforced with randomly multidirectionally arranged continuous carbon fibers (fiber content approx. 55%) according to the invention to stress compared to a PEEK implant according to WO 2014/198421 A1.

Material and Methods:

Two simplified cylindrical implant models were created. The first implant model only consisted of one component (1-C) which was made of PEEK reinforced with 55% randomly multidirectionally arranged continuous carbon fibers (55-CFR-PEEK) and matched an implant according to the invention.

The second implant model consisted of two components (2-C): An implant core made of the same PEEK type as the 1-C implant model (55-CFR-PEEK) and an implant shell which had a layer thickness of 0.5 mm in the surface area of the implant and consisted of a TiO2-filled PEEK. FIGS. 1A and 1B show a longitudinal sectional view of the two implants examined, 1-C and 2-C.

The two implants 1-C and 2-C were each embedded in a bone segment and provided with an abutment, an abutment screw, and an implant crown of a first lower molar (FIGS. 2A and 2B). The implant crown and the abutment consisted of the same TiO2-filled PEEK type as the implant shell of the 2-C implant. The abutment screw was also made of 55-CPR-PEEK.

Table 1 summarizes the materials used. It was assumed for the analysis that the materials were isotropic and linear-elastic.

TABLE 1

Properties of the materials used.

| Material | Modulus E [GPa] | Poisson Ratio |
|---|---|---|
| $TiO_2$-filled PEEK (20% $TiO_2$) | 4.1 | 0.4 |
| PEEK reinforced with 55% randomly multidirectionally arranged continuous carbon fibers (55-CFR-PEEK) | 40 | 0.35 |
| Cortical bone | 13.4 | 0.3 |
| Cancellous bone | 1.37 | 0.31 |

Then the joint properties between the contact pairs of the components were defined (Table 2).

TABLE 2

Joint condition between individual contact pairs.

| Joint | Contact pair | | Condition |
|---|---|---|---|
| 1 | Crown | Abutment | Bonded contact, perfectly bonded |
| 2 | Screw head | Abutment | Rough contact |
| 3 | Screw head washer | Abutment | Bonded contact, perfectly bonded |
| 4 | Screw shaft | Abutment | Rough contact |
| 5 | Abutment | Implant | Rough contact |
| 6 | Screw thread | Female implant thread | Bonded contact, perfectly bonded |
| 7 | Implant core | Implant shell | Bonded contact, perfectly bonded |
| 8 | Implant shell | Bone | Rough contact |
| 9 | Cortical bone | Cancellous bone | Bonded contact, perfectly bonded |

Then a predominantly hexahedral finite element mesh was created with element types Tet10, Hex20, Wed15, and pyr13 and a refinement in the interface regions. For the C-1 model, it consisted of 137,425 elements and 498,543 nodes, and for the C-2 model, it consisted of 143,210 elements and 530,334 nodes (FIG. 3).

Then a load of 100 N was introduced into the implant crown at an angle of 30° to the longitudinal axis of the implant in accordance with ISO 14801:2007 (FIG. 4), and the surface contact pressures and deformations in the peri-implant bone were analyzed.

Findings:

The findings of surface contact pressures and deformations in the peri-implant bone when exposing the implants to stress are summarized in Table 3.

TABLE 3

Summary of findings for the maximum overall deformation of the peri-implant bone and the maximum contact pressures at the implant-bone interface at variable moduli E of the PEEK portions reinforced with continuous carbon fibers

| | One-component implant (1-C) | | Two-component implant (2-C) | |
|---|---|---|---|---|
| Modulus E of the 55-CFR-PEEK portion [MPa] | Maximum overall deformation of the bone [μm] | Maximum contact pressure at the implant-bone interface [MPa] | Maximum overall deformation of the bone [μm] | Maximum contact pressure at the implant-bone interface [MPa] |
| 40 | 9.4 | 51.9 | 11 | 56.7 |

CONCLUSIONS

It was surprisingly found that a one-component implant (1-C) according to the invention, when exposed to a load, has advantageous properties with respect to its impact on the bone compared to a two-component implant (2-C) according to WO 2014/198421 A1. When the 1-C implant was used, the maximum overall deformation of the bone was lower and the maximum contact pressure at the implant-bone interface was reduced compared to a 2-C implant.

The invention claimed is:

1. A single component implant made of a plastic material, comprising a homogenous thermoplastic material which is reinforced with targeted multidirectionally arranged long fibers and has a modulus of elasticity E of 30-50 GPa, wherein the reinforcing fibers have a diameter of 4 to 10 µm and the targeted multidirectional arrangement of the fibers is calculated based on patient data collected, wherein the collected patient data include at least one of: the force applied under mechanical stress, the bone density, or the spatial structure of the environment into which an implant is to be inserted.

2. The single component implant according to claim 1, wherein at least one of orientation of the fibers, fiber content, type of fibers or fiber diameter differs in a plurality of sections within the single component implant.

3. The single component implant according to claim 1, wherein the thermoplastic material is PEEK.

4. The single component implant according to claim 1, wherein the reinforcing fibers are carbon fibers, glass fibers, zirconia fibers, alumina fibers, silicon carbide fibers, or mixtures thereof.

5. The single component implant according to claim 1, wherein a fiber content of the homogenous thermoplastic material is 10-80% by volume.

6. The single component implant according to claim 1, wherein the fiber-reinforced homogenous thermoplastic material contains compound additives of titanium dioxide, magnesium oxide, magnesium sulfate, hydroxyl apatite, tricalcium phosphate, bioglass, calcium sulfate, zinc phosphate, zinc oxide, magnesium phosphate or a combination thereof.

7. The single component implant according to claim 6, wherein the compound additives are present only in a surface area of the single component implant up to a depth of 200 µm.

8. The single component implant according to claim 1, wherein the single component implant is a dental implant.

9. The single component implant according to claim 1, wherein a fiber content of the homogenous thermoplastic material is 40-60% by volume.

10. A system for producing a customized single component implant having a modulus of elasticity E of 30-50 GPa according to claim 1, the system comprising:
a device for collecting patient data regarding an environment into which the single component implant is to be inserted, wherein the patient data particularly includes any of:
a force applied under mechanical stress,
a bone density, and
a spatial structure of the environment,
a computer program for creating a model for the single component implant based on the patient data collected, wherein:
a three-dimensional structure of the single component implant,
a material composition including a homogenous thermoplastic material, reinforcing long fibers having a diameter of 4 to 10 µm, and
a targeted multidirectional arrangement of the reinforcing long fibers is calculated, and
a device for producing the customized single component implant based on the created model, the customized single component implant being produced by 3D printing laser sintering, or a combination thereof.

11. A device for producing a customized single component implant having a modulus of elasticity E of 30-50 GPa according to claim 1, the device comprising:
a unit for collecting patient data regarding an environment into which the single component implant is to be inserted, wherein the patient data particularly includes any of:
a force applied under mechanical stress,
a bone density, and
a spatial structure of the environment,
a unit for creating a model for the single component implant based on the patient data collected, wherein:
a three-dimensional structure of the single component implant,
a material composition including a homogenous thermoplastic material, reinforcing long fibers having a diameter of 4 to 10 µm, and
a targeted multidirectional arrangement of the reinforcing long fibers is calculated, and
a unit for producing the customized single component implant based on the created model, the customized single component implant being produced by 3D printing, laser sintering, or a combination thereof.

12. A method for producing a customized single component implant having a modulus of elasticity E of 30-50 GPa according to claim 1, comprising:
collecting patient data regarding an environment into which the single component implant is to be inserted, wherein the patient data particularly includes any of:
a force applied under mechanical stress,
a bone density, and
a spatial structure of the environment,
creating a model for the customized single component implant based on the patient data collected, wherein:
a three-dimensional structure of the single component implant,
a material composition including a homogenous thermoplastic material, reinforcing long fibers having a diameter of 4 to 10 µm, and
a targeted multidirectional arrangement of the reinforcing long fibers is calculated, and
producing the customized single component implant based on the created model by 3D printing, laser sintering, or a combination thereof.

* * * * *